US009107688B2

(12) United States Patent
Kimball et al.

(10) Patent No.: US 9,107,688 B2
(45) Date of Patent: Aug. 18, 2015

(54) ACTIVATION FEATURE FOR SURGICAL INSTRUMENT WITH PENCIL GRIP

(75) Inventors: Cory G. Kimball, Cincinnati, OH (US); Daniel W. Price, Loveland, OH (US); William E. Clem, Bozeman, MT (US)

(73) Assignee: Ethicon Endo-Surgery, Inc., Cincinnati, OH (US)

(*) Notice: Subject to any disclaimer, the term of this patent is extended or adjusted under 35 U.S.C. 154(b) by 0 days.

(21) Appl. No.: 13/426,834

(22) Filed: Mar. 22, 2012

(65) Prior Publication Data
US 2012/0203213 A1 Aug. 9, 2012

Related U.S. Application Data

(63) Continuation-in-part of application No. 12/557,799, filed on Sep. 11, 2009.

(60) Provisional application No. 61/096,500, filed on Sep. 12, 2008.

(51) Int. Cl.
*A61B 17/32* (2006.01)
*H01H 15/00* (2006.01)
(Continued)

(52) U.S. Cl.
CPC ............ *A61B 17/320068* (2013.01); *A61B 2017/00017* (2013.01); *A61B 2017/00367* (2013.01);
(Continued)

(58) Field of Classification Search
CPC ............. A61B 17/320068; A61B 2017/00017; A61B 2017/00367; H01H 15/04; H01H 15/06; H01H 13/10; H01H 13/13; H01H 15/005
USPC ............ 606/39–45, 169; 200/5 D, 64, 277.2, 200/339, 553–563, 600, 16 D, 176, 178, 200/519, 531, 536, 547, 549
See application file for complete search history.

(56) References Cited

U.S. PATENT DOCUMENTS 2,715,169 A * 8/1955 High .................... 200/262
3,968,467 A   7/1976 Lampen et al.
(Continued)

FOREIGN PATENT DOCUMENTS

DE   36 00 990    7/1987
EP   1 852 078    11/2007
(Continued)

OTHER PUBLICATIONS

International Search Report dated May 3, 2010 for Application No. PCT/US09/056616.
(Continued)

*Primary Examiner* — Kathleen Holwerda
(74) *Attorney, Agent, or Firm* — Frost Brown Todd LLC

(57) ABSTRACT

An exemplary surgical instrument comprises a handpiece, an end effector, and an activation and control feature that is operable to selectively activate an end effector and select an energy level for the end effector. One version of the activation and control feature includes a "floating" button feature where activation and control is accomplished based on the displacement of the button from a home position. In some versions the activation and control feature is sealed within the handpiece, but controllable by the user's touch with the handpiece. The sealed configuration can allow the handpiece to be sterilizable, e.g., using steam sterilization. The activation and control feature may comprise capacitive switches, resistive sensors, resonant cavity switching technology, infrared sensing technology, technology that uses a resonant standing wave on a surface that is perturbed by the presence of a finger, and/or any other suitable type of technology.

13 Claims, 14 Drawing Sheets

(51) Int. Cl.
  *H01H 15/06* (2006.01)
  *A61B 17/00* (2006.01)
  *A61B 18/00* (2006.01)
  *A61C 1/00* (2006.01)
  *A61C 1/07* (2006.01)

(52) U.S. Cl.
  CPC .............. *A61B2017/00424* (2013.01); *A61B 2018/00916* (2013.01); *A61C 1/0015* (2013.01); *A61C 1/07* (2013.01); *H01H 15/005* (2013.01); *H01H 15/06* (2013.01)

(56) References Cited

U.S. PATENT DOCUMENTS

| | | | |
|---|---|---|---|
| 4,221,975 A | | 9/1980 | Ledniczki et al. |
| 4,659,879 A * | | 4/1987 | Hasegawa .................. 200/5 A |
| 5,015,227 A * | | 5/1991 | Broadwin et al. ............ 604/22 |
| 5,217,478 A | | 6/1993 | Rexroth |
| 5,324,299 A | | 6/1994 | Davison et al. |
| 5,555,004 A * | | 9/1996 | Ono et al. .................. 345/161 |
| 5,873,873 A | | 2/1999 | Smith et al. |
| 6,258,088 B1 * | | 7/2001 | Tzonev et al. ............... 606/42 |
| 6,344,619 B1 * | | 2/2002 | Yamasaki et al. ............ 200/6 A |
| 6,423,082 B1 | | 7/2002 | Houser et al. |
| 6,500,176 B1 | | 12/2002 | Truckai et al. |
| 6,608,263 B2 * | | 8/2003 | Myojin ...................... 200/16 D |
| 6,666,875 B1 | | 12/2003 | Sakurai et al. |
| 6,752,816 B2 | | 6/2004 | Culp et al. |
| 6,773,444 B2 | | 8/2004 | Messerly |
| 6,945,981 B2 | | 9/2005 | Donofrio et al. |
| 7,112,201 B2 | | 9/2006 | Truckai et al. |
| 7,125,409 B2 | | 10/2006 | Truckai et al. |
| 7,169,146 B2 | | 1/2007 | Truckai et al. |
| 7,186,253 B2 | | 3/2007 | Truckai et al. |
| 7,189,233 B2 | | 3/2007 | Truckai et al. |
| 7,220,951 B2 | | 5/2007 | Truckai et al. |
| 7,309,849 B2 | | 12/2007 | Truckai et al. |
| 7,311,709 B2 | | 12/2007 | Truckai et al. |
| 7,354,440 B2 | | 4/2008 | Truckai et al. |
| 7,381,209 B2 | | 6/2008 | Truckai et al. |
| 7,416,101 B2 | | 8/2008 | Shelton, IV et al. |
| 7,609,178 B2 | | 10/2009 | Son et al. |
| 7,738,971 B2 | | 6/2010 | Swayze et al. |
| 7,878,981 B2 | | 2/2011 | Strother et al. |
| 7,951,162 B2 | | 5/2011 | Murphy et al. |
| 8,047,103 B2 * | | 11/2011 | Davidson et al. .......... 81/177.85 |
| 8,139,035 B2 | | 3/2012 | Strawn et al. |
| 8,152,825 B2 | | 4/2012 | Madan et al. |
| 8,172,838 B2 | | 5/2012 | Schnitzler |
| 2002/0049464 A1 * | | 4/2002 | Donofrio et al. .............. 606/169 |
| 2004/0116952 A1 | | 6/2004 | Sakurai et al. |
| 2006/0079874 A1 | | 4/2006 | Faller et al. |
| 2007/0191713 A1 | | 8/2007 | Eichmann et al. |
| 2007/0282333 A1 | | 12/2007 | Fortson et al. |
| 2008/0173530 A1 * | | 7/2008 | Adachi ....................... 200/561 |
| 2008/0200940 A1 | | 8/2008 | Eichmann et al. |
| 2009/0143797 A1 | | 6/2009 | Smith et al. |
| 2009/0209990 A1 | | 8/2009 | Yates et al. |
| 2010/0069940 A1 | | 3/2010 | Miller et al. |
| 2011/0015660 A1 | | 1/2011 | Wiener et al. |
| 2011/0087218 A1 | | 4/2011 | Boudreaux et al. |
| 2012/0078247 A1 | | 3/2012 | Worrell et al. |
| 2012/0116367 A1 | | 5/2012 | Houser et al. |
| 2012/0116379 A1 | | 5/2012 | Yates et al. |
| 2012/0116388 A1 | | 5/2012 | Houser et al. |
| 2012/0116396 A1 | | 5/2012 | Price et al. |
| 2012/0210223 A1 | | 8/2012 | Eppolito |

FOREIGN PATENT DOCUMENTS

| | | |
|---|---|---|
| EP | 2 215 981 | 8/2010 |
| JP | 62-68447 | 3/1987 |
| JP | 2007-54665 | 3/2007 |
| JP | 2008-55151 | 3/2008 |
| WO | WO 2008/089174 | 7/2008 |

OTHER PUBLICATIONS

International Preliminary Report on Patentability dated Mar. 15, 2011 for Application No. PCT/US2009/056616.
Partial European Search Report dated Jun. 19, 2013 for Application No. EP 13160723.
Chinese Office Action dated Dec. 28, 2012 for Application No. CN 200980136024.7.
Japanese Office Action, Notification of Reasons for Refusal, dated Oct. 29, 2013 for Application No. 2011-526986.

* cited by examiner

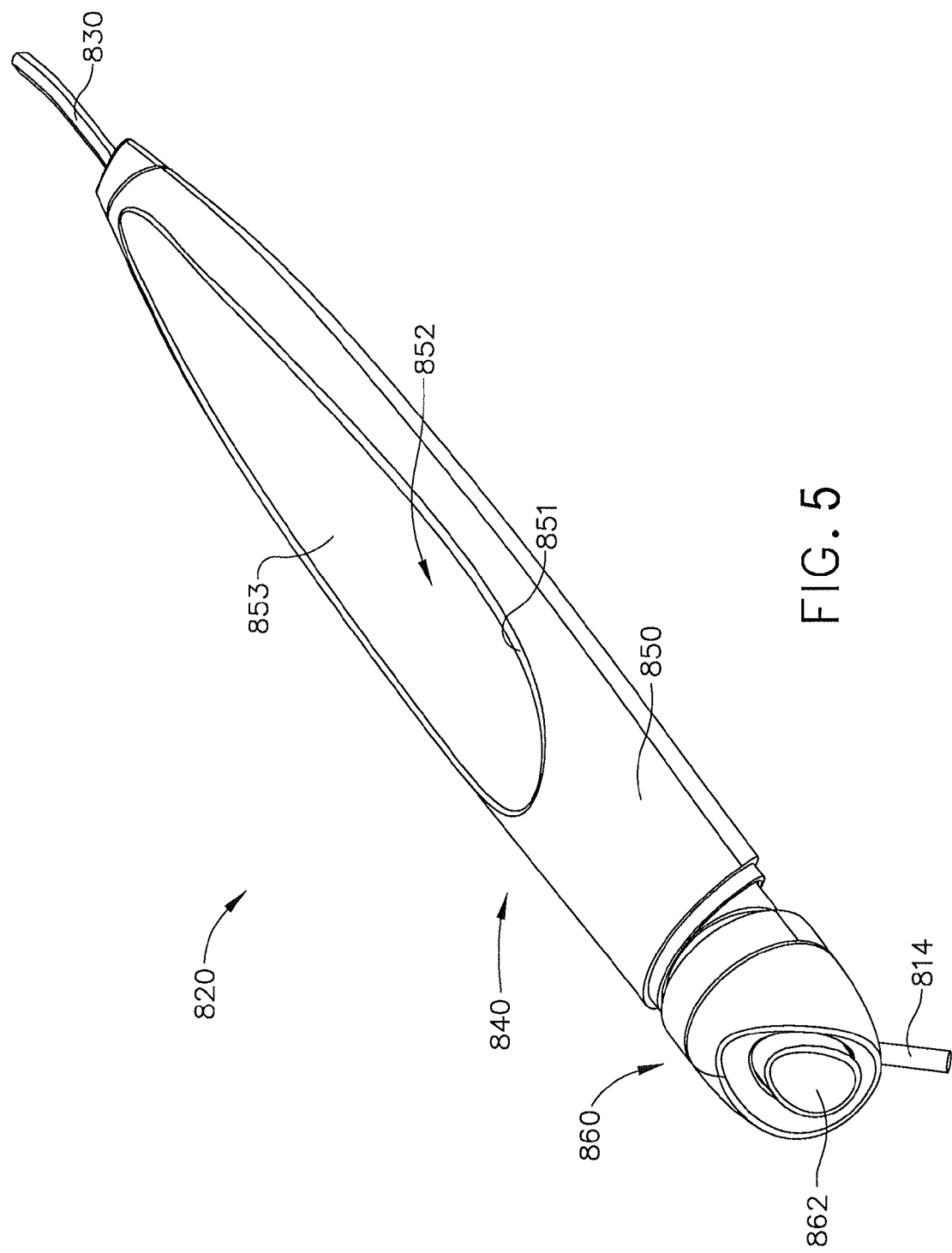

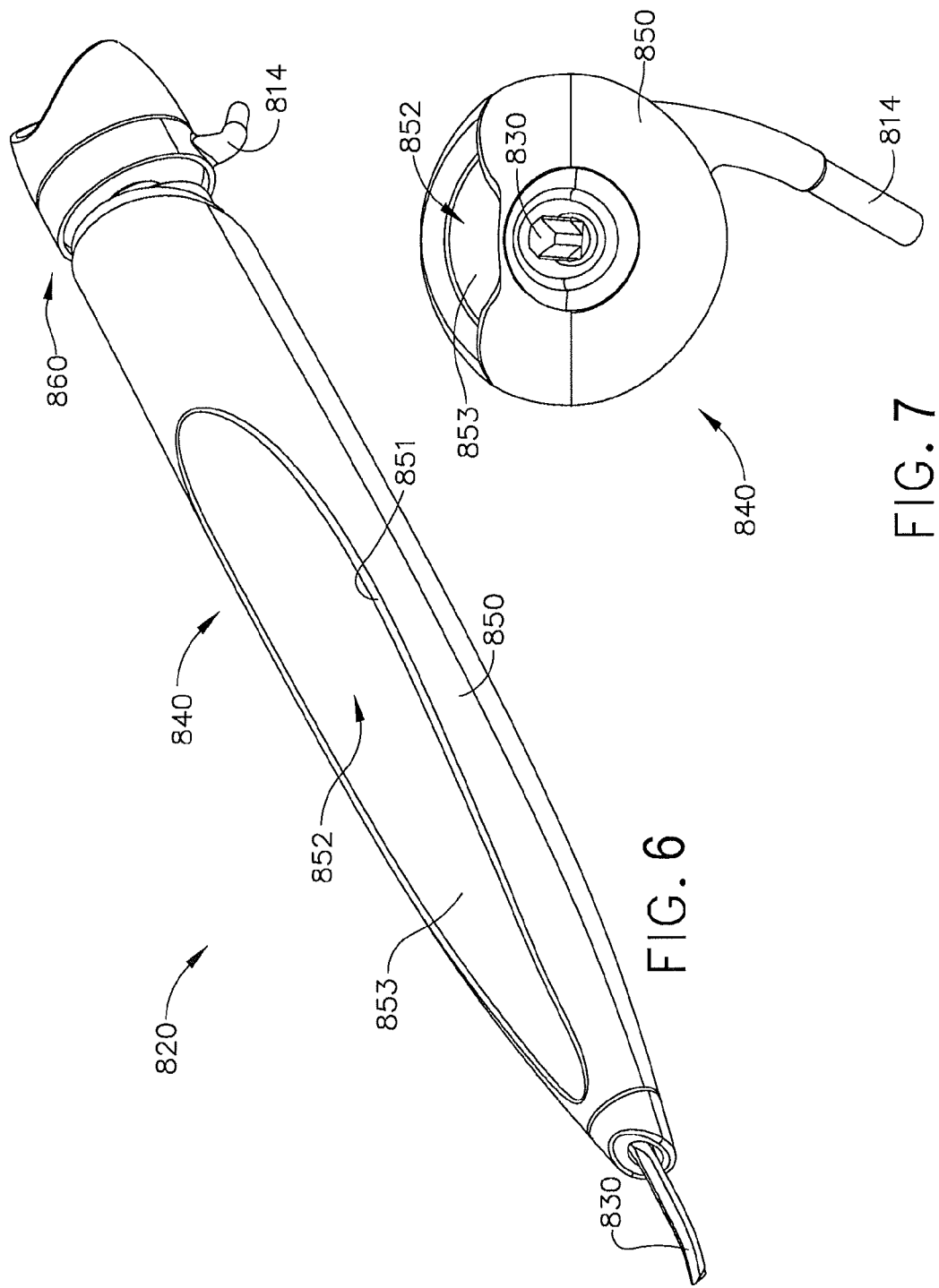

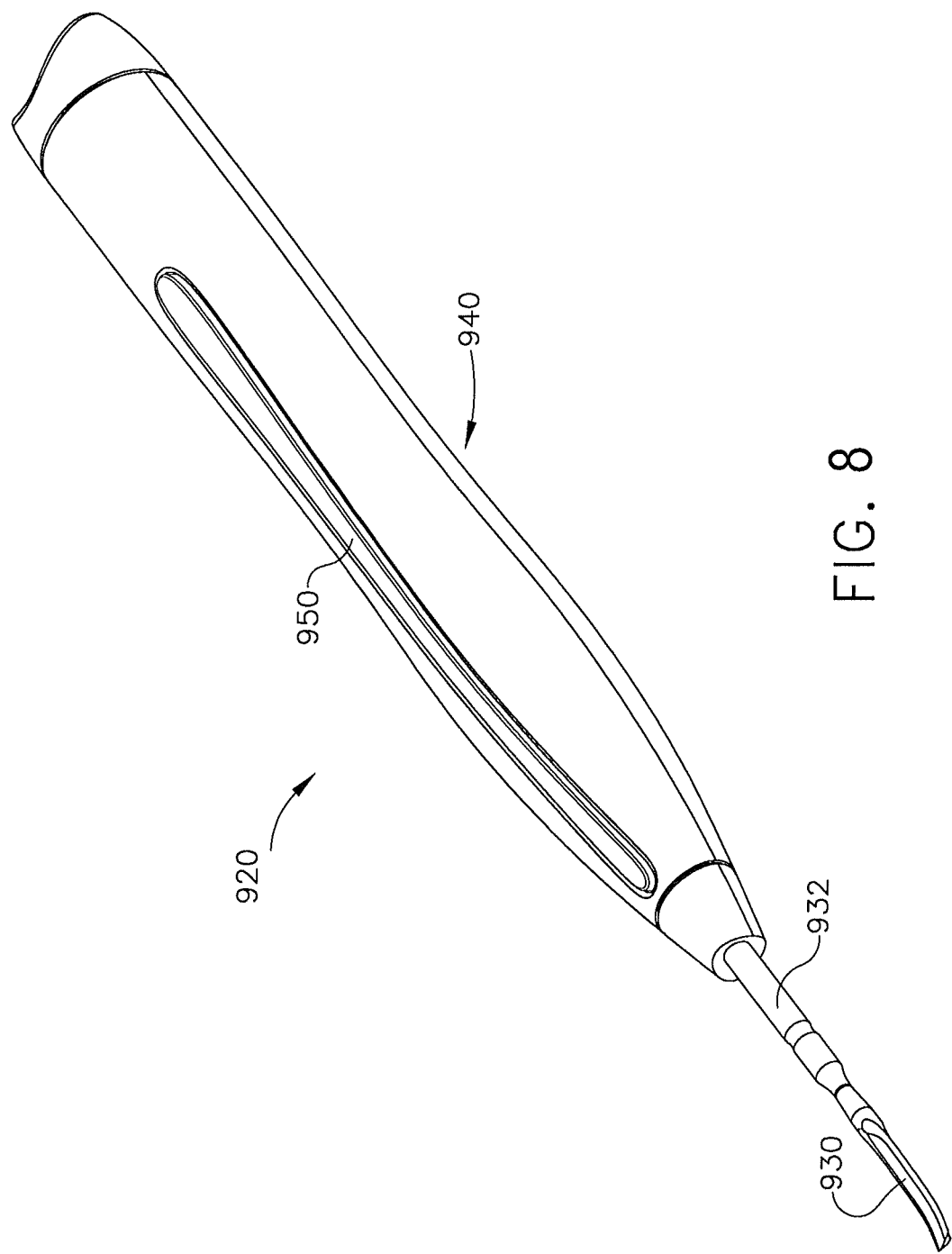

ACTIVATION FEATURE FOR SURGICAL INSTRUMENT WITH PENCIL GRIP

PRIORITY

This application claims priority to, and is a continuation-in-part of, U.S. patent application Ser. No. 12/557,799, filed Sep. 11, 2009, entitled "Ultrasonic Device for Fingertip Control," and published Mar. 18, 2010 as U.S. Pub. No. 2010/0069940, issued as U.S. Pat. No. 9,023,071 on May 5, 2015, the disclosure of which is incorporated by reference herein, and which further claims priority to U.S. Provisional Patent Application Ser. No. 61/096,500, filed Sep. 12, 2008, entitled "Ultrasonic Device for Fingertip Control," the disclosure of which is incorporated by reference herein.

BACKGROUND

Some versions of the present invention generally relate to ultrasonic surgical systems. For instance, some versions relate to an ultrasonic device that allows surgeons to perform cutting, coagulation, and/or fine dissection, such as may be required in fine and delicate surgical procedures such as plastic surgery, etc. It should be understood, that the teachings herein may be readily applied to various other types of devices and systems, and need not be limited to the ultrasonic surgical setting.

Ultrasonic surgical instruments may provide substantially simultaneous cutting of tissue and homeostasis by coagulation, which may minimize patient trauma. The cutting action may be realized by an end-effector, or blade tip, at the distal end of the instrument, which transmits ultrasonic energy to tissue brought into contact with the end-effector. Ultrasonic instruments of this nature can be configured for open surgical use, laparoscopic or endoscopic surgical procedures including robotic-assisted procedures, or other types of uses or procedures. Performing a plastic surgery procedure (e.g. abdominoplasty, breast reconstruction/reduction, face lift, etc.) may involve significant recovery time for the patient and risk of post-operative complications such as seroma and hematoma. The recovery time may include additional office visits post-operatively, which may affect patient satisfaction and/or decrease the amount of time a surgeon is available for surgery. In some settings, advanced energy instruments (in lieu of traditional monopolar electrosurgery—"bovie") may provide a less complicated recovery experience and potentially shorten the post-operative recovery time. However, conventional advanced energy instruments may not be suitable for plastic surgery procedures.

Some surgical instruments utilize ultrasonic energy for both precise cutting and controlled coagulation. Ultrasonic energy may cut and coagulate by using lower temperatures than those used by conventional electrosurgery. Vibrating at high frequencies (e.g., 55,500 times per second), the ultrasonic blade may denature protein in the tissue to form a sticky coagulum. Pressure exerted on tissue with the blade surface may collapse blood vessels and allow the coagulum to form a hemostatic seal. The precision of cutting and coagulation may be controlled by the surgeon's technique and adjusting the power level, blade edge, tissue traction and blade pressure, etc. Some conventional ultrasonic surgical devices may utilize a foot pedal to energize the surgical instrument. The surgeon may operate such a foot pedal to activate a generator that provides energy that is transmitted to the cutting blade for cutting and coagulating tissue while the surgeon simultaneously applies pressure to the handle to press the blade against the tissue. In some settings, the surgeon may lose focus on the surgical field while the surgeon searches for the foot pedal. The foot pedal may also get in the way of the surgeon's movement during a procedure and/or contribute to surgeon leg fatigue (e.g., during long procedures). Some uses of an ultrasonic surgical instrument may include the user using the handpiece of the instrument to apply force to tissue with the blade, even if the blade is not being ultrasonically activated (e.g., "blunt dissection").

Some conventional ultrasonic surgical devices may have finger actuation of the power at discrete locations along the length of the device. This may make it difficult to move the instrument distally and proximally to gain depth or more control. It may also require the use of a thumbwheel and/or release button to adjust the blade angle, rather than by merely rotating the wrist or rotating the entire device as if the device were a pencil. At least some conventional ultrasonic surgical devices may provide no sensory feedback to the user indicating that the end effector is energized other than momentary switch haptics. The sound created by the end effector may be above the range of human hearing and there may be no tactile vibration in the handpiece. Conventional methods of indicating the active state include an audible beep emitted by the generator. Additional, more instantaneous and local indication of activation could be achieved with visible lighting on the handpiece, audible sound feedback emanated from the handpiece, and/or haptic vibration of the handpiece.

Many types of power activation are known for various devices requiring switch control. Capacitive actuation occurs when a sensor recognizes a change in the dielectric constant of its immediate environment. A commercial example of this is the QTOUCH sensor by Atmel Corporation of San Jose, Calif. In some settings, such sensors or switches may present a risk of inadvertent activation. For instance, a capacitive switch may be inadvertently activated by fluid inadvertently spilled on the surface of the capacitive switch; or by placement of a device incorporating the capacitive switch on a surface, such that the surface activates the capacitive switch. It may therefore be desirable in certain circumstances to differentiate between intentional and unintentional activation; and/or to reduce the likelihood of (if not prevent) unintentional activation of a capacitive switch or similar switch.

One form of resistive technology is the strain gauge. The resistive properties of piezoelectric flouropolymers (PVDF) are a function of applied pressure or strain. In other words, the measured resistance is a function of applied pressure. Actuation is triggered when the applied pressure exceeds a threshold. Another form of resistive technology measures the resistance across a plane of pressure sensitive material; or utilizes the scheme developed by Transparent Products, Inc. of Valencia, Calif. A combination of resistive and capacitive sensing can be used to enhance the sensitivity and tactile feedback while reducing inadvertent activation. A capacitive sensor may require no force, only the presence of the finger to change the dielectric field. A resistive sensor may provide confirmation that a finger (e.g., rather than an accidental fluid) is the source of the dielectric change. Resonant cavity switching technology is offered by ITW ActiveTouch (a division of Illinois Tool Works Inc.) of Buffalo Grove, Ill. Other switching technology may include infrared response to the tip of the human finger to actuate. Still other switching technology may use a resonant, standing wave on a surface that is perturbed by the presence of a finger.

While a variety of surgical instruments have been made and used, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 5 depicts a perspective view of another exemplary ultrasonic surgical device, having a rotatable sheath and an elongate control and activation surface;

FIG. 6 depicts another perspective view of the ultrasonic surgical device of FIG. 5;

FIG. 7 depicts an end view of the ultrasonic surgical device of FIG. 5;

FIG. 8 depicts a perspective view of another exemplary ultrasonic surgical device, having an elongate control and activation surface;

Figure 1:
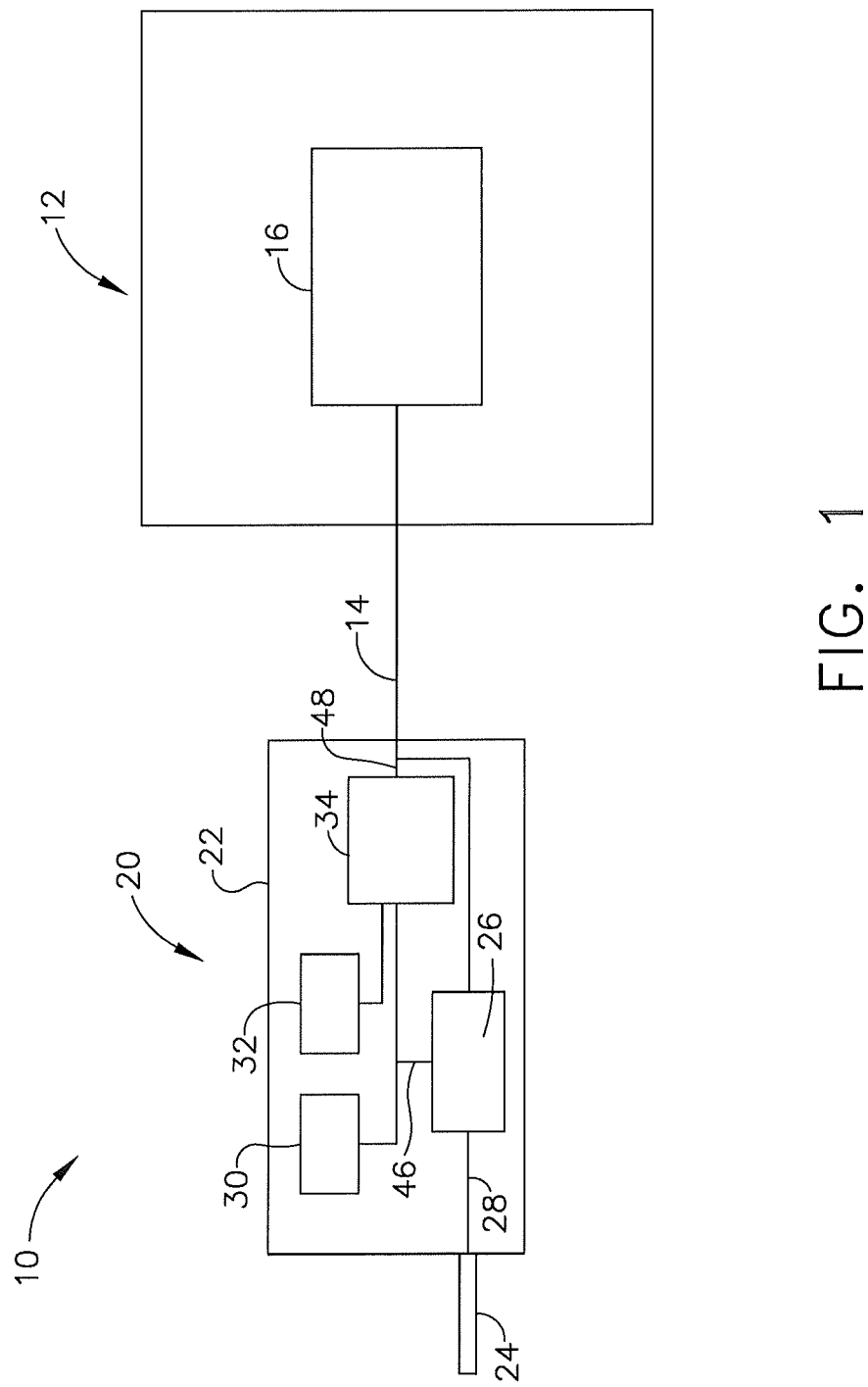
FIG. 1 depicts a block schematic view of an exemplary ultrasonic surgical system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive. Further, it is understood that any one or more of the following-described embodiments, expressions of embodiments, versions, examples, etc. can be combined with or modified in accordance with any one or more of the other following-described embodiments, expressions of embodiments, versions, examples, etc.

I. Overview

Several examples described herein are particularly directed to an improved ultrasonic surgical instrument, which is configured for effecting tissue dissecting, cutting, coagulation, and/or clamping of tissue during surgical procedures, including delicate surgical procedures, such as plastic surgery. Several examples described herein are configured for use in open surgical procedures, but may also be used in other types of surgery, including but not limited to laparoscopic surgery. Versatile use is facilitated by selective use of ultrasonic energy. When ultrasonic components of the apparatus are inactive, tissue can be manipulated, as desired, without tissue cutting or damage. When the ultrasonic components are activated, ultrasonic energy may provide for both tissue cutting and coagulation.

Further, the below examples are described in terms of a blade-only instrument. This feature is not intended to be limiting, as the examples disclosed herein may have equal application in clamp coagulator instruments as are exemplarily disclosed in U.S. Pat. Nos. 5,873,873 and 6,773,444, the disclosures of which are incorporated by reference herein.

As mentioned previously, it should be understood, that the teachings herein may be readily applied to various other types of devices and systems, and need not be limited to the ultrasonic surgical setting. Examples of endoscopic surgical instruments where the teachings herein can be applied include those instruments disclosed in U.S. Pat. No. 7,416, 101 entitled "Motor-Driven Surgical Cutting and Fastening Instrument with Loading Force Feedback," issued Aug. 26, 2008, the disclosure of which is incorporated by reference herein; U.S. Pat. No. 7,738,971 entitled "Post-Sterilization Programming of Surgical Instruments," issued Jun. 15, 2010, the disclosure of which is incorporated by reference herein; U.S. Pub. No. 2006/0079874 entitled "Tissue Pad for Use with an Ultrasonic Surgical Instrument," published Apr. 13, 2006, the disclosure of which is incorporated by reference herein; U.S. Pub. No. 2007/0191713 entitled "Ultrasonic Device for Cutting and Coagulating," published Aug. 16, 2007, the disclosure of which is incorporated by reference herein; U.S. Pub. No. 2007/0282333 entitled "Ultrasonic Waveguide and Blade," published Dec. 6, 2007, the disclosure of which is incorporated by reference herein; U.S. Pub. No. 2008/0200940 entitled "Ultrasonic Device for Cutting and Coagulating," published Aug. 21, 2008, the disclosure of which is incorporated by reference herein; U.S. Pub. No. 2009/0209990 entitled "Motorized Surgical Cutting and Fastening Instrument Having Handle Based Power Source," published Aug. 20, 2009, issued as U.S. Pat. No. 8,657,174 on Feb. 25, 2014, the disclosure of which is incorporated by reference herein; U.S. Pub. No. 2010/0069940 entitled "Ultrasonic Device for Fingertip Control," published Mar. 18, 2010, issued as U.S. Pat. No. 9,023,071 on May 5, 2015, the disclosure of which is incorporated by reference herein; U.S.

Pub. No. 2011/0015660, entitled "Rotating Transducer Mount for Ultrasonic Surgical Instruments," published Jan. 20, 2011, and issued Jun. 11, 2013 as U.S. Pat. No. 8,461,744, the disclosure of which is incorporated by reference herein; U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein; U.S. Pub. No. 2011/0087218, entitled "Surgical Instrument Comprising First and Second Drive Systems Actuatable by a Common Trigger Mechanism," published Apr. 14, 2011, issued as U.S. Pat. No. 8,939,974 on Jan. 27, 2015, the disclosure of which is incorporated by reference herein; U.S. patent application Ser. No. 13/151,481, entitled "Motor Driven Electrosurgical Device with Mechanical and Electrical Feedback," filed Jun. 2, 2011, and published May 10, 2012 as U.S. Pub. No. 2012/0116379, the disclosure of which is incorporated by reference herein; U.S. patent application Ser. No. 13/269,870, entitled "Surgical Instrument with Modular Shaft and End Effector," filed Oct. 10, 2011, and published May 10, 2012 as U.S. Pub. No. 2012/0116388, the disclosure of which is incorporated by reference herein; U.S. patent application Ser. No. 13/235,660, entitled "Articulation Joint Features for Articulating Surgical Device," filed Sep. 19, 2011, and published Mar. 29, 2012 as U.S. Pub. No. 2012/0078247, the disclosure of which is incorporated by reference herein; U.S. patent application Ser. No. 13/274,805, entitled "Surgical Instrument with Modular End Effector," filed Oct. 17, 2011, and published May 10, 2012 as U.S. Pub. No. 2012/0116396, issued as U.S. Pat. No. 8,998,939 on Apr. 7, 2015 the disclosure of which is incorporated by reference herein; and U.S. patent application Ser. No. 13/276,725, entitled "Medical Device Usage Data Processing," filed Oct. 19, 2011, and published May 10, 2012 as U.S. Pub. No. 2012/0116367, the disclosure of which is incorporated by reference herein. Also, various ways in which medical devices, including surgical instruments, may be adapted to include a portable power source are disclosed in U.S. Provisional Application Ser. No. 61/410,603, filed Nov. 5, 2010, entitled "Energy-Based Surgical Instruments," the disclosure of which is incorporated by reference herein.

As will become apparent from the following description, exemplary surgical instruments described herein may be particularly configured for disposable use by virtue of straightforward construction. As such, it is contemplated that the some versions of the surgical instruments be used in association with an ultrasonic generator unit of a surgical system, whereby ultrasonic energy from the generator unit provides the desired ultrasonic actuation for the surgical instrument. It will be appreciated that surgical instruments embodying the principles of the present invention may be configured for non-disposable or multiple use and/or non-detachably integrated with an associated ultrasonic generator unit.

In some versions of instruments described herein, the surgical instrument includes a re-useable, sterilizable, handpiece that is configured to connect with various styles or types of end effectors. These various styles or types of end effectors can be designed as single-use disposable components, or in some versions re-useable and sterilizable components. In some versions that include a re-useable, sterilizable, handpiece, the activation components, e.g., the power switch and power level switch, are sealed within the handpiece housing such that steam sterilization can be used without damaging the electronics of the activation components. While in some cases this handpiece with sealed activation components is used with detachable end effectors, in other cases, the handpiece having sealed activation components can be used in instruments that incorporate non-detachable end effectors. Further description of such sealed activation components is provided in later sections.

Also, in some versions having a re-useable, sterilizable, handpiece for use with different types of end effectors, the handpiece and end effectors can contain certain electronic features, e.g., chips, that communicate with each other. For instance, a first chip in a portion of the selected end effector can communicate with a second chip in the handpiece such that the control circuitry associated with the handpiece knows which end effector is installed, and further how to provide power to that end effector. By way of further example, another chip can be included in the cable that connects the handpiece to a universal generator such that the cable chip can tell the generator whether a radio frequency handpiece is being used or whether an ultrasonic handpiece is being used. It should therefore be understood that a "universal" handpiece and/or cable may be used with various kinds of end effectors, including those having different configurations, different shaft lengths, and/or different surgical modalities (e.g. ultrasonic, electrosurgical, stapling, etc.).

FIG. 1 shows components of an exemplary surgical system (10) in diagrammatic block form. As shown, system (10) comprises an ultrasonic generator (12) and an ultrasonic surgical instrument (20). Generator (12) and instrument (20) are coupled together via cable (14). Cable (14) may comprise a plurality of wires, and may provide unidirectional electrical communication from generator (12) to instrument (20) and/or bidirectional electrical communication between generator (12) and instrument (20). By way of example only, cable (14) may comprise a "hot" wire for electrical power to surgical instrument (20), a ground wire, and a signal wire for transmitting signals from surgical instrument (20) to ultrasonic generator (12), with a shield surrounding the three wires. In some versions, separate "hot" wires are used for separate activation voltages (e.g., one "hot" wire for a first activation voltage and another "hot" wire for a second activation voltage, or a variable voltage between the wires proportional to the power requested, etc.). Of course, any other suitable number or configuration of wires may be used. By way of example only, generator (12) may comprise the GEN04 (also referred to as Generator 300) sold by Ethicon Endo-Surgery, Inc. of Cincinnati, Ohio. Alternatively, any other suitable generator (12) may be used. As will be described in greater detail below, generator (12) is operable to provide power to instrument (20) to perform ultrasonic surgical procedures.

Instrument (20) comprises a handpiece (22), which is configured to be grasped in one hand (or two hands) of a user and manipulated by one hand (or two hands) of the user during a surgical procedure. For instance, in some versions, handpiece (22) may be grasped like a pencil by the user. In some other versions, handpiece (22) may be grasped like scissors by the user. Of course, handpiece (22) may be configured to be gripped in any other suitable fashion. A blade (24) extends distally from the handpiece (22). Handpiece (22) includes an ultrasonic transducer (26) and an ultrasonic waveguide (28), which couples ultrasonic transducer (26) with blade (24). Ultrasonic transducer (26) receives electrical power from generator (12) via cable (14), as will be described in greater detail below. By virtue of its piezoelectric properties, ultrasonic transducer (26) is operable to convert such electrical power into ultrasonic vibrational energy. By way of example only, ultrasonic transducer (26) may be constructed and operable in accordance with the teachings of U.S. Pub. No. 2007/0106158, entitled "Medical Ultrasound System and Handpiece and Methods for Making and Tuning," published May 10, 2007, and issued Apr. 10, 2012 as U.S. Pat. No. 8,152,825, the disclosure of which is incorporated by reference herein. Alternatively, any other suitable ultrasonic transducer (26) may be used.

Ultrasonic waveguide (28) may be flexible, semi-flexible, rigid, or have any other suitable properties. As noted above, ultrasonic transducer (26) is integrally coupled with blade (24) via ultrasonic waveguide (28). In particular, when ultrasonic transducer (26) is activated to vibrate at ultrasonic frequencies, such vibrations are communicated through ultrasonic waveguide (28) to blade (24), such that blade (24) will also vibrate at ultrasonic frequencies. In some versions, ultrasonic waveguide (28) may amplify the mechanical vibrations transmitted through ultrasonic waveguide (28) to blade (24). Ultrasonic transducer (26), ultrasonic waveguide (28), and blade (24) together thus form an acoustic assembly providing ultrasonic energy for surgical procedures when powered by generator (12). Handpiece (22) is configured to substantially isolate the user from the vibrations of this acoustic assembly.

Ultrasonic waveguide (28) may further have features to control the gain of the longitudinal vibration along ultrasonic waveguide (28) and/or features to tune ultrasonic waveguide (28) to the resonant frequency of the system. For instance, ultrasonic waveguide (28) may have any suitable cross-sectional dimension, such as a substantially uniform cross-section, be tapered at various sections, be tapered along its entire length, or have any other suitable configuration. Ultrasonic waveguide (28) may, for example, have a length substantially equal to an integral number of one-half system wavelengths ($n\lambda/2$). Ultrasonic waveguide (28) and blade (24) may be fabricated from a solid core shaft constructed out of a material or combination of materials that propagates ultrasonic energy efficiently, such as titanium alloy (i.e., Ti-6Al-4V), aluminum alloys, sapphire, stainless steel, or any other acoustically compatible material or combination of materials.

In some versions, ultrasonic waveguide (28) and blade (24) comprise product code HF105 or product code DH105, each of which is sold by Ethicon Endo-Surgery, Inc. of Cincinnati, Ohio. By way of example only, ultrasonic waveguide (28) and/or blade (24) may be constructed and operable in accordance with the teachings of U.S. Pat. No. 6,423,082, entitled "Ultrasonic Surgical Blade with Improved Cutting and Coagulation Features," issued Jul. 23, 2002, the disclosure of which is incorporated by reference herein. As another merely illustrative example, ultrasonic waveguide (28) and/or blade (24) may be constructed and operable in accordance with the teachings of U.S. Pat. No. 5,324,299, entitled "Ultrasonic Scalpel Blade and Methods of Application," issued Jun. 28, 1994, the disclosure of which is incorporated by reference herein. Other suitable properties and configurations of ultrasonic waveguide (28) and blade (24) will be apparent to those of ordinary skill in the art in view of the teachings herein.

Handpiece (22) of the present example also includes a control selector (30) and an activation switch (32), which are each in communication with a circuit board (34). By way of example only, circuit board (34) may comprise a conventional printed circuit board, a flex circuit, a rigid-flex circuit, or may have any other suitable configuration. Control selector (30) and activation switch (32) may be in communication with circuit board (34) via one or more wires, traces formed in a circuit board or flex circuit, and/or in any other suitable fashion. Circuit board (34) is coupled with cable (14), which is in turn coupled with control circuitry (16) within generator (12). Activation switch (32) is operable to selectively activate power to ultrasonic transducer (26). In particular, when switch (32) is activated, such activation provides communication of appropriate power to ultrasonic transducer (26) via cable (14). Several examples of forms that activation switch (32) may take will be described in greater detail below; while other various forms that activation switch (32) may take will be apparent to those of ordinary skill in the art in view of the teachings herein.

In the present example, surgical system (10) is operable to provide at least two different levels or types of ultrasonic energy (e.g., different frequencies and/or amplitudes, etc.) at blade (24). To that end, control selector (30) is operable to permit the user to select a desired level/amplitude of ultrasonic energy. Several examples of forms that control selector (30) may take will be described in greater detail below; while other various forms that control selector (30) may take will be apparent to those of ordinary skill in the art in view of the teachings herein. In some versions, when a user makes a selection through control selector (30), the user's selection is communicated back to control circuitry (16) of generator (12) via cable (14), and control circuitry (16) adjusts the power communicated from generator (12) accordingly. It should be understood that the level/amplitude of ultrasonic energy provided at blade (24) may be a function of characteristics of the electrical power communicated from generator (12) to instrument (20) via cable (14). Thus, control circuitry (16) of generator (12) may provide electrical power having characteristics associated with the selected ultrasonic energy level/amplitude or type, via cable (14). Generator (12) may thus be operable to communicate different types or degrees of electrical power to ultrasonic transducer (26), in accordance with selections made by the user via control selector (30). In particular, and by way of example only, generator (12) may increase the voltage and/or current of the applied signal to increase the longitudinal amplitude of the acoustic structure. As a merely illustrative example, generator (12) may provide selectability between a "level 1" and a "level 5," which may correspond with a blade (24) vibrational resonance amplitude of approximately 50 microns and approximately 90 microns, respectively. Various ways in which control circuitry (16) may be configured will be apparent to those of ordinary skill in the art in view of the teachings herein.

Figure 2:
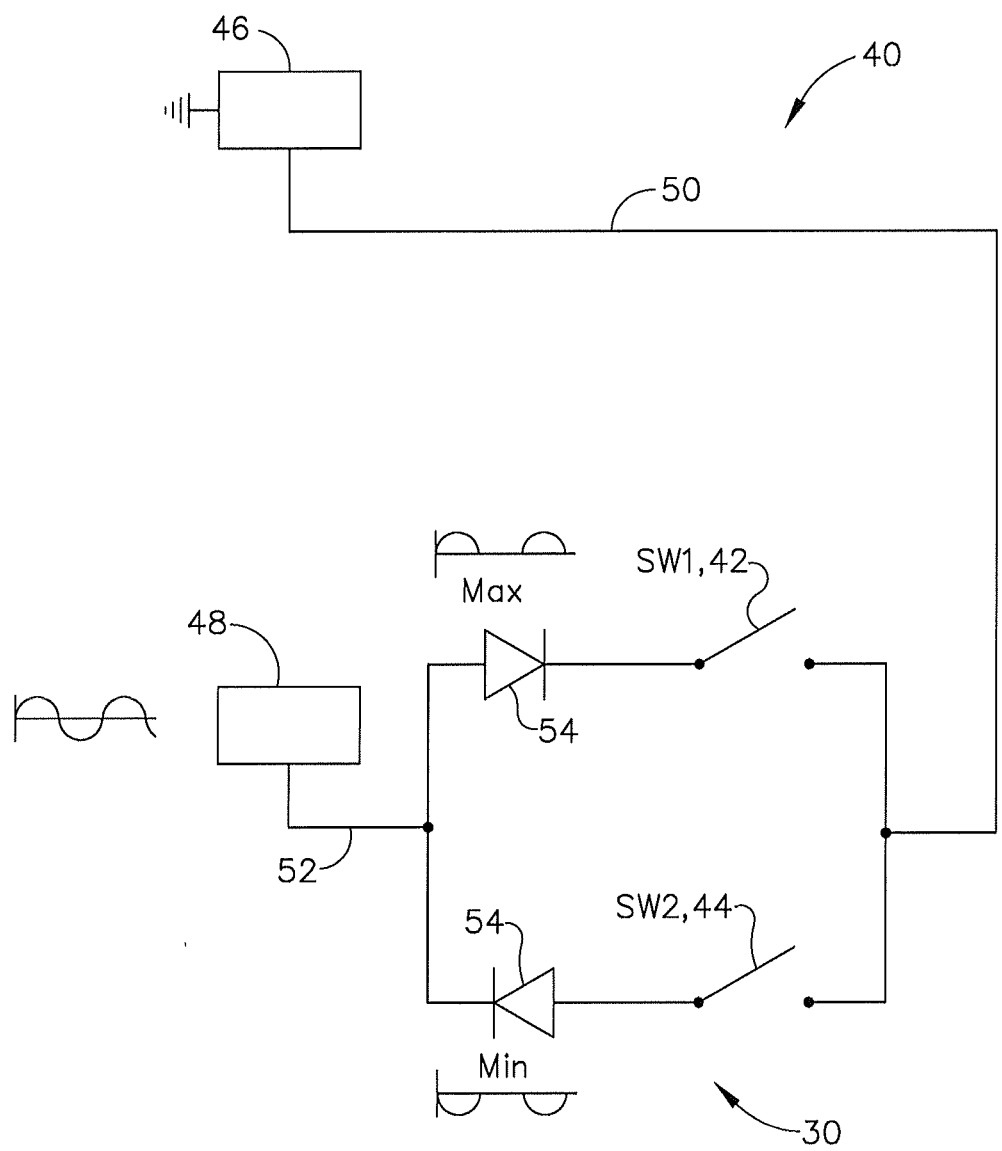
FIG. 2 depicts an electrical schematic of an exemplary hand switch circuit.

FIG. 2 depicts an exemplary circuit (40) that may be incorporated into handpiece (22) to provide selectability of ultrasonic energy for blade (24). In some versions, circuit (40)

provides an electro-mechanical interface between control selector (30) and generator (12) via ultrasonic transducer (26). It should also be understood that at least a portion of circuit (40) may be incorporated into circuit board (34) in some versions. In this example, control selector (30) includes a first switch (42) that is operable to select a "maximum" level of ultrasonic energy for blade (24) and a second switch (44) that is operable to select a "minimum" level of ultrasonic energy for blade (24). While this particular example includes just two different levels of ultrasonic energy to select from, it will be apparent from the teachings below that control selector (30) may alternatively provide more than two different levels of ultrasonic energy to select from, including but not limited to a virtually infinitely variable level of ultrasonic energy within a predetermined range. It should also be understood that first and second switches (42, 44) collectively form at least part of control selector (30) in the present example. First switch (42) comprises a dome switch and second switch (44) also comprises a dome switch in this example, though any other suitable types of switches or components may be used.

Pin (48) is electrically coupled with the control signal wire from circuit board (34) to control circuitry (16) of generator (12); while pin (46) is electrically coupled with ground. Pin (46) is also coupled with control selector (30) via a conductor (50); while pin (48) is also coupled with control selector (30) via a conductor (52). In some versions, pin (46) provides a shared ground between control selector (30) and ultrasonic transducer (26). When either switch (42, 44) is activated (e.g., closed), the activated switch (42, 44) provides an electrical signal to generator (12) to activate blade (24). Circuit (40) also comprises two diodes within a diode package (54). As will be recognized by those of ordinary skill in the art, diode package (54) provides modification to a control signal communicated to generator (12), which provides modification to the electrical power received by transducer (26), which in turn provides modification to the ultrasonic action of blade (24) in accordance with the user's selections. Of course, the foregoing features and configuration of circuit (40) are merely illustrative. Circuit (40) and/or other components of handpiece (20) may otherwise be configured in accordance with the teachings of U.S. Pub. No. 2007/0191713, entitled "Ultrasonic Device for Cutting and Coagulating," published Aug. 16, 2007, the disclosure of which is incorporated by reference herein; and/or the teachings of U.S. Pub. No. 2008/0200940, entitled "Ultrasonic Energy Device for Cutting and Coagulating," published Aug. 21, 2008, the disclosure of which is incorporated by reference herein. Various other suitable features and configurations of circuit (40) will be apparent to those of ordinary skill in the art in view of the teachings herein.

In some alternative versions, control circuitry (16) is located within handpiece (22). For instance, in some such versions, generator (12) only communicates one type of electrical power (e.g., just one voltage and/or current available) to handpiece (22), and control circuitry (16) within handpiece (22) is operable to modify the electrical power (e.g., the voltage of the electrical power), in accordance with selections made by the user via control selector (30), before the electrical power reaches ultrasonic transducer (26). It should be understood that in some such versions, cable (14) may be omitted entirely. In still other alternative versions, generator (12) is essentially incorporated into handpiece (22) along with all other components of surgical system (10). For instance, one or more batteries (not shown) or other portable sources of power may be provided in handpiece (22). An example of a self-contained ultrasonic surgical device is disclosed in U.S. Pat. No. 6,666,875, entitled "Surgical Apparatus Permitting Recharge of Battery-Driven Surgical Instrument in Noncontact State," issued Dec. 23, 2003, the disclosure of which is incorporated by reference herein. Still other suitable ways in which the components depicted in FIG. 1 may be rearranged or otherwise configured or modified will be apparent to those of ordinary skill in the art in view of the teachings herein.

The following discussion relates to various exemplary components and configurations for instrument (20) and components thereof. It should be understood that the various examples of instrument (20) described below may be readily incorporated into a surgical system (10) as described above. It should also be understood that the various components and operability of instrument (20) described above may be readily incorporated into the exemplary versions of instrument (20) described below. Various suitable ways in which the above and below teachings may be combined will be apparent to those of ordinary skill in the art in view of the teachings herein.

II. Exemplary Ultrasonic Surgical Instrument with Extendable End

Figure 3:
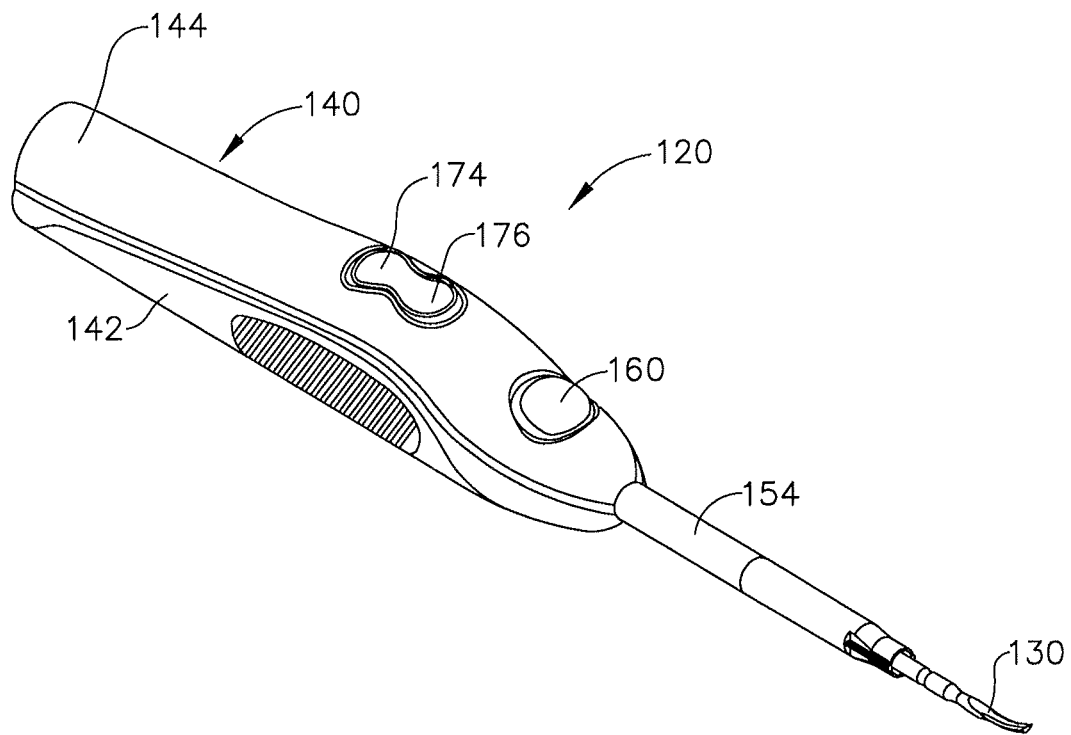
FIG. 3 depicts a perspective view of an exemplary ultrasonic surgical device.
Figure 4:
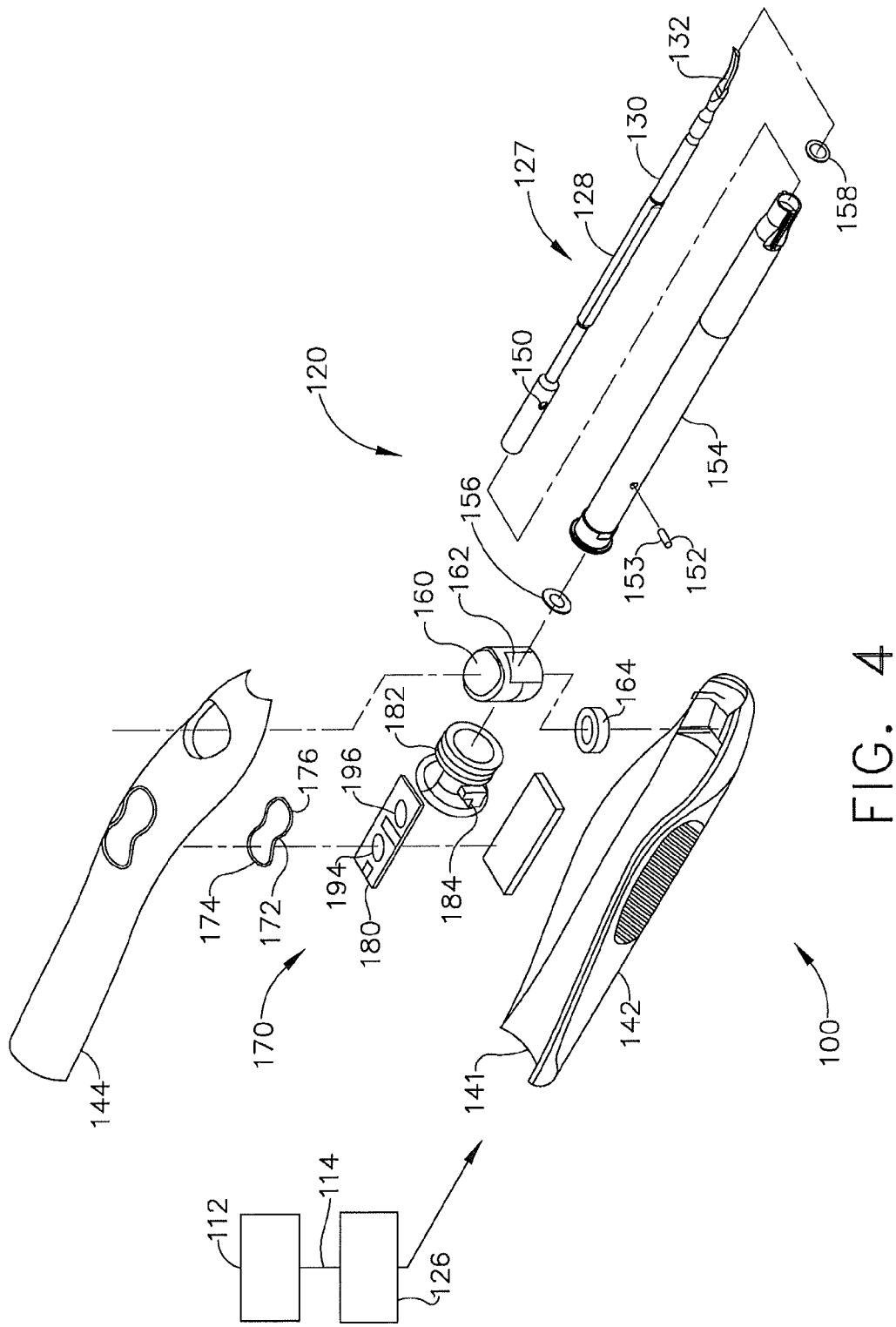
FIG. 4 depicts an exploded view of the ultrasonic surgical device of FIG. 3.

FIGS. 3-4 depict an exemplary ultrasonic surgical instrument (120), which is part of an ultrasonic surgical system (110) that includes an ultrasonic transducer (126) coupled with an ultrasonic generator (112) via a cable (114). Instrument (120) also includes an ultrasonic transmission assembly (127), which is coupled with ultrasonic transducer (126). In some versions, ultrasonic transmission assembly (127) is coupled with ultrasonic transducer (126) by a threaded connection, though any other suitable type of coupling may be used. Ultrasonic transmission assembly (127) comprises an ultrasonic waveguide (128) and blade (130). As will be apparent to those of ordinary skill in the art, when ultrasonic transducer (126) is powered by generator (112), ultrasonic transducer (126) produces ultrasonic vibrations, which are communicated to blade (130) via ultrasonic waveguide (128). This causes tip (132) of blade (130) to vibrate at an ultrasonic frequency, allowing blade (130) to be used to cut and coagulate tissue, etc.

Instrument (120) further comprises a multi-piece handle assembly (140) that is configured to substantially isolate the user from the vibrations of the acoustic assembly contained within transducer (126). By way of example only, handle assembly (140) may be shaped to be held by a user in a conventional manner, but it is contemplated that instrument (120) principally be grasped and manipulated in a pencil-like arrangement. Handle assembly (140) of the present example comprises mating housing portions (142) and (144). While a multi-piece handle assembly (140) is illustrated, handle assembly (140) may alternatively comprise a single or unitary component. Handle assembly (140) may be constructed from a durable plastic, such as polycarbonate or a liquid crystal polymer. It is also contemplated that handle assembly (140) may alternatively be made from a variety of materials or combinations of materials, including but not limited to other plastics, ceramics, and/or metals, etc. In some versions, the proximal end of instrument (120) receives and is fitted with ultrasonic transducer (126) by insertion of ultrasonic transducer (126) into handle assembly (140). Instrument (120) may be attached to and removed from ultrasonic transducer (126) as a unit. The elongated transmission assembly (127) of the instrument (120) extends orthogonally from instrument handle assembly (140).

Ultrasonic waveguide (128), which is adapted to transmit ultrasonic energy from transducer (126) to the tip (132) of blade (130), may be flexible, semi-flexible or rigid. Ultrasonic waveguide (128) may also be configured to amplify the mechanical vibrations transmitted through ultrasonic waveguide (128) to blade (130). Ultrasonic waveguide (128) may further include at least one radial hole or aperture (150) extending therethrough, substantially perpendicular to the longitudinal axis of ultrasonic waveguide (128). Aperture (150), which may be positioned at a node, is configured to receive a connector pin (152), discussed below, which connects ultrasonic waveguide (128) to an outer sheath (154). Proximal o-ring (156) and distal o-ring (158) are assembled onto transmission assembly (127) near the nodes in the present example, though various other components or configurations may be used.

Blade (130) may be integral with ultrasonic waveguide (128) and formed as a single unit. In some versions, blade (130) may be connected by a threaded connection, a welded joint, or other coupling mechanisms. The distal end of blade (130), or blade tip (132), is disposed near an anti-node in order to tune the acoustic assembly to a preferred resonant frequency $f_o$ when the acoustic assembly is not loaded by tissue. When ultrasonic transducer (126) is energized, blade tip (132) is configured to move substantially longitudinally (along the x axis) in the range of, for example, approximately 10 to 500 microns peak-to-peak, and perhaps in the range of about 20 to about 200 microns, at a predetermined vibrational frequency $f_o$ of, for example, 55,500 Hz. Blade tip (132) may also vibrate in the y-axis at about 1 to about 10 percent of the motion in the x-axis. Of course, movement of blade tip (132) may alternatively have any other suitable characteristics.

Ultrasonic waveguide (128) is positioned within outer sheath (154) and held in place via pin (152). Pin (152) may be made of any compatible metal, such as stainless steel or titanium or a durable plastic, such as polycarbonate or a liquid crystal polymer. Alternatively, any other suitable material or combination of materials may be used. In some versions, pin (152) is partially coated with an elastomeric material, such as silicon, etc., for that portion (153) of pin (152) that extends through ultrasonic waveguide (128). Elastomeric material may provide insulation from the vibrating blade throughout the length of hole (152). In some settings, this may enable high efficiency operation whereby minimal overheating is generated and maximum ultrasonic output power is available at blade tip (132) for cutting and coagulation, etc. Of course, such elastomeric material is merely optional.

Outer sheath (154) passes through an aperture (162) of release button (160). Positioned below release button (160) and within housing portion (142) is a spring (164) that asserts an upward force on release button (160). The upward force causes the perimeter of aperture (162) to firmly assert pressure against outer sheath (154), and thereby selectively prevents outer sheath (154), ultrasonic waveguide (128), and blade (130) from either rotating within handle (140) or axially translating with respect to handle (140). When the user exerts a downward force on release button (160), spring (164) is compressed and it no longer asserts a holding force on outer sheath (154). The user may then axially translate outer sheath (154), ultrasonic waveguide (128), and blade (130) relative to handle (140) and/or rotate outer sheath (154), ultrasonic waveguide (128), and blade (130) relative to handle (140). Accordingly, it should be understood that the longitudinal and/or rotational position of blade (130) relative to handle (140) may be selectively changed by the user, while still allowing blade (130) to vibrate ultrasonically at such selected positions, allowing blade (130) to be used in various surgical procedures at such selected positions. To initiate such ultrasonic action of blade (130), the user may operate a footswitch (not shown), activate a pushbutton (174, 176) as described below, activate a button on generator (112), or perform some other act on some component of system (100).

In the present example, housing of handle (140) includes a proximal end, a distal end, and a cavity (141) extending longitudinally therein. Cavity (141) is configured to accept a switch assembly (170) and ultrasonic transducer assembly (126). In one some versions, the distal end of ultrasonic transducer assembly (126) threadedly attaches to the proximal end of ultrasonic waveguide (128), though any other suitable type of coupling may be used. The distal end of ultrasonic transducer (126) also interfaces with switch assembly (170) to provide the surgeon with finger-activated controls on surgical instrument (120). Ultrasonic transducer (126) of the present example includes two conductive rings (not shown) which are securely disposed within the body of ultrasonic transducer (126) as is described in U.S. Pub. No. 2007/0106158, entitled "Medical Ultrasound System and Handpiece and Methods for Making and Tuning," published May 10, 2007, issued as U.S. Pat. No. 8,152,825 on Apr. 10, 2012, the disclosure of which is incorporated by reference herein. Switch assembly (170) of the present example comprises a pushbutton assembly (172), a circuit assembly (180), a switch housing (182), a first pin conductor (184), and a second pin conductor (not shown). Switch housing (182) is annular-shaped and is supported within handle assembly (140) by way of corresponding supporting mounts on switch housing (182) and housing portions (142, 144).

Pushbutton assembly (172) of the present example comprises pushbuttons (174, 176). Circuit assembly (180) provides for the electro-mechanical interface between pushbuttons (174, 176) and generator (112) via ultrasonic transducer (126). Circuit assembly (180) comprises two dome switches (194, 196) that are mechanically actuated by depressing pushbuttons (174, 176) respectively. Dome switches (194, 196) are electrical contact switches, that when depressed provide an electrical signal to generator (112). Pins (not shown) are electrically connected to dome switches (194, 196). In particular, one end of each pin is electrically connected to a corresponding dome switch (194, 196). The other end of each pin is electrically connected with a corresponding ring conductor at the distal end of ultrasonic transducer (126). That is, the pins each have spring-loaded tips that interface with ultrasonic transducer (126) in a manner similar to that described above. Circuit assembly (180) also comprises two diodes within a diode package (not shown) that connect to the pins, respectively. While the pins provide electrical contact to the ring conductors of ultrasonic transducer, the ring conductors are in turn connected to conductors in cable (114) that connects to generator (112). Of course a variety of alternative configurations may be used.

As is readily apparent, by depressing pushbuttons (174, 176) the corresponding contact surfaces depress against corresponding dome switches (194, 196) to selectively activate the circuit (180). For instance, when the surgeon depresses pushbutton (174), generator (112) may respond with a certain energy level, such as a maximum ("max") power setting. When the surgeon depresses pushbutton (176), generator (112) may respond with a certain energy level, such as a minimum ("min") power setting, which conforms to accepted industry practice for pushbutton location and the corresponding power setting. Instrument (120) may further be configured and operable in accordance with the teachings of U.S. Pub. No. 2008/0200940, entitled "Ultrasonic Energy Device for Cutting and Coagulating," published Aug. 21, 2008, the disclosure of which is incorporated by reference herein. Alternatively, instrument (120) may be provided with a variety of other components, configurations, and/or types of operability.

III. Exemplary Ultrasonic Surgical Instrument with Rotatable Control and Activation Member FIGS. 5-7 depict another exemplary ultrasonic surgical instrument (820), comprising a blade (830) positioned distally relative to a handpiece (840). An ultrasonic transducer (not shown) is secured in handpiece (840), and may be coupled with an ultrasonic generator (not shown) in accordance with the teachings herein. An ultrasonic waveguide (not shown) couples the ultrasonic transducer with blade (830) in accordance with the teachings herein. It should therefore be understood that an ultrasonic generator may be used to activate the ultrasonic transducer of handpiece (840), and that the activated ultrasonic transducer may transmit ultrasonic vibration to blade (830) via the ultrasonic waveguide in accordance with the teachings herein. Handpiece (840) may be configured to substantially isolate the hand of the user relative to these ultrasonic vibrations. It should also be understood that ultrasonically vibrating blade (830) may be used to perform a variety of surgical procedures. Various other components that may be incorporated into handpiece (840), including but not limited to various components and configurations of electric circuitry, will be apparent to those of ordinary skill in the art in view of the teachings herein.

Instrument (820) of the present example further comprises a housing shell (850), a control member (852), and a tail section (860). Tail section (860) comprises an activation button (862), and has a cable (814) that is coupled with the ultrasonic generator. Housing shell (850), control member (852), and tail section (860) are all independently rotatable relative to each other. That is, housing shell (850) is rotatable relative to control member (852) and tail section (860); control member (852) is rotatable relative to housing shell (850) and tail section (860); and tail section (860) is rotatable relative to housing shell (850) and control member (852). Control member (852) is integrally secured relative to the ultrasonic transducer and relative to blade (830). Thus, when control member (852) is rotated relative to housing shell (850) and/or tail section (860), the ultrasonic transducer and blade (830) rotate unitarily with control member (852). It should be understood that handpiece (840) may include various types of bearings or other features, in various locations, to facilitate the above-described relative rotation while also providing structural support. Furthermore, since tail section (860) (and hence, cable (814)) and control member (852) are rotatable relative to each other, and since control member is unitary with the ultrasonic transducer in this example, slip rings or other components may be included to provide continuous electrical contact despite such relative rotation. In particular, the ultrasonic transducer may be electrically coupled with cable (814) by slip rings or similar components. Similarly, control member (852) may be electrically coupled with cable (814) by slip rings or similar components.

Control member (852) of the present example presents an external surface (853) that may be contacted by the user's hand during use of instrument (840). Housing shell (850) defines an opening (851) that exposes a region of external surface (853), allowing external surface (853) to be contacted by a user's finger or hand. It should be understood that external surface (853) extends about the full circumference of control member (852), such that external surface (853) may be contacted by the user's finger or hand through opening (851) regardless of the rotational position of housing shell (850) relative to control member (852). While the term "circumference" may be used to refer to a dimension of the outer perimeter of control member (852), this should not be read as requiring control member (852) to be cylindrical. While control member (852) may in fact be cylindrical in some versions, control member (852) may alternatively have a variety of other shapes and configurations, including but not limited to tapered or frusto-conical, etc.

Control member (852) is configured such that it is responsive to the location at which the user's hand touches external surface (853). In particular, control member (852) is configured such that the level of ultrasonic energy applied to blade (830) is based at least in part on the longitudinal position at which the user touches external surface (853). For instance, a user touching external surface (853) near the distal end of opening (851) may result in ultrasonic activation of blade (830) at a "maximum" level of ultrasonic energy; while a user touching external surface (853) near the proximal end of opening (851) may result in ultrasonic activation of blade (830) at a "minimum" level of ultrasonic energy. In some versions, control member (852) simply provides selectability between a "minimum" and "maximum" level of ultrasonic energy. In some other versions, control member (852) also provides selectability of ultrasonic energy levels between the "minimum" and "maximum" level, such as when the user touches surface (853) somewhere within the middle region of opening (851). In some such versions, the available energy levels are discrete and predetermined. For instance, as the user moves their hand or finger longitudinally along external surface (853) from the distal end of opening (851) toward the proximal end of opening (851), the ultrasonic energy level may start at the "maximum" level and decrease in stepped increments in accordance with the longitudinal position of the user's hand or finger on external surface (853). Discrete energy levels may thus be associated with discrete longitudinal ranges of length along external surface (853).

In some other versions, the available ultrasonic energy levels may be virtually infinitely variable within a predetermined range. For instance, the ultrasonic energy level may be a substantially linear function of the longitudinal position of the user's hand or finger along the length of external surface (853), such that the ultrasonic energy level progressively and substantially continuously increases or decreases as the user's hand or finger is slid along external surface (853). Still other suitable ways in which the ultrasonic energy level of blade (830) may be based at least in part on the longitudinal position of the user's hand or finger along external surface (853) will be apparent to those of ordinary skill in the art in view of the teachings herein.

It should be understood that various types of technologies may be incorporated into control member (852) to allow it to sense and react to the longitudinal position at which the user's hand touches external surface (853). For instance, control member (852) may comprise a plurality of capacitive switches; a plurality of resistive sensors; resonant cavity switching technology; infrared sensing technology; technology that uses a resonant, standing wave on a surface that is perturbed by the presence of a finger; and/or any other suitable type of technology. In some versions, an array of resistive sensors, infrared sensors, or other types of sensors may be provided in control member (852), to provide substantially continuous sensing of and reaction to the longitudinal position of the user's finger or hand along external surface (853). Control member (852) and associated components may also be configured to discriminate between a user's single finger (e.g., for controlling the energy level for blade (830), etc.) and the hand or multiple fingers of the user (e.g., for activating blade (830) at the selected energy level, etc.). Still other suitable types of and arrangements of switches, sensors, or other technology that may be incorporated into control member (852) will be apparent to those of ordinary skill in the art in view of the teachings herein. Various ways in which such various types of control member (852) components may be incorporated into the circuitry of instrument (820), as well as various circuit components that may accompany or be coupled with variations of control member (852), will also be apparent to those of ordinary skill in the art in view of the teachings herein. By way of example only, a variable resistor and/or some other type(s) of circuit component(s) may be responsive to the longitudinal position of a user's hand or finger along control member (852), and may provide a virtually infinitely variable level of electrical power (within a predefined range) to the ultrasonic transducer in the handpiece (840), which may thereby provide a virtually infinitely variable level of ultrasonic energy (within a predefined range) at blade (830).

Activation button (862) is operable to selectively activate the ultrasonic transducer, to thereby selectively activate blade (830) at the level selected using control member (852). For instance, activation button (862) may act as a switch selectively coupling the ultrasonic transducer with the ultrasonic generator. Activation button (862) may take a variety of forms. By way of example only, activation button (862) may comprise a conventional electromechanical button, a capacitive switch; a resistive sensor; resonant cavity switching technology; infrared sensing technology; technology that uses a resonant, standing wave on a surface that is perturbed by the presence of a finger; and/or any other suitable type of technology. Still other suitable types of switches, sensors, or other technology that may be incorporated into activation button (862) will be apparent to those of ordinary skill in the art in view of the teachings herein. Various ways in which such various types of activation button (862) components may be incorporated into the circuitry of instrument (820), as well as various circuit components that may accompany or be coupled with variations of activation button (862), will also be apparent to those of ordinary skill in the art in view of the teachings herein.

In some other versions of instrument (820), activation button (862) is omitted, such that activation and ultrasonic energy level selection are both provided through control member (852). For instance, instrument (820) may be configured such that as soon as a user touches external surface (853), such touching may simultaneously effect selection of an ultrasonic energy level (e.g., in accordance with the longitudinal position at which external surface (853) is touched) and activation of blade (830). As another merely illustrative example, instrument (820) may be configured such that the role of control member (852) as ultrasonic energy level selector or blade (830) activator is based at least in part on the way in which the user touches external surface (853). For instance, the user may select an ultrasonic energy level by sliding their finger along external surface (853) to a longitudinal position associated with a desired ultrasonic energy level; then activate blade (830) by tapping or double-tapping external surface (853). As another non-limiting example, ultrasonic energy level selection may be based on a number of taps on external surface (853) (e.g., more taps provides higher ultrasonic energy level); while activation of blade (830) is effected through touching external surface (853) for at least a certain duration of time (e.g., three seconds). Alternatively, any other suitable combination of touching external surface (853), sliding against external surface (853), tapping against external surface (853), etc., may be used to provide selection of an ultrasonic energy level and/or activation of blade (830). Such alternatives will be apparent to those of ordinary skill in the art in view of the teachings herein.

Figure 13:
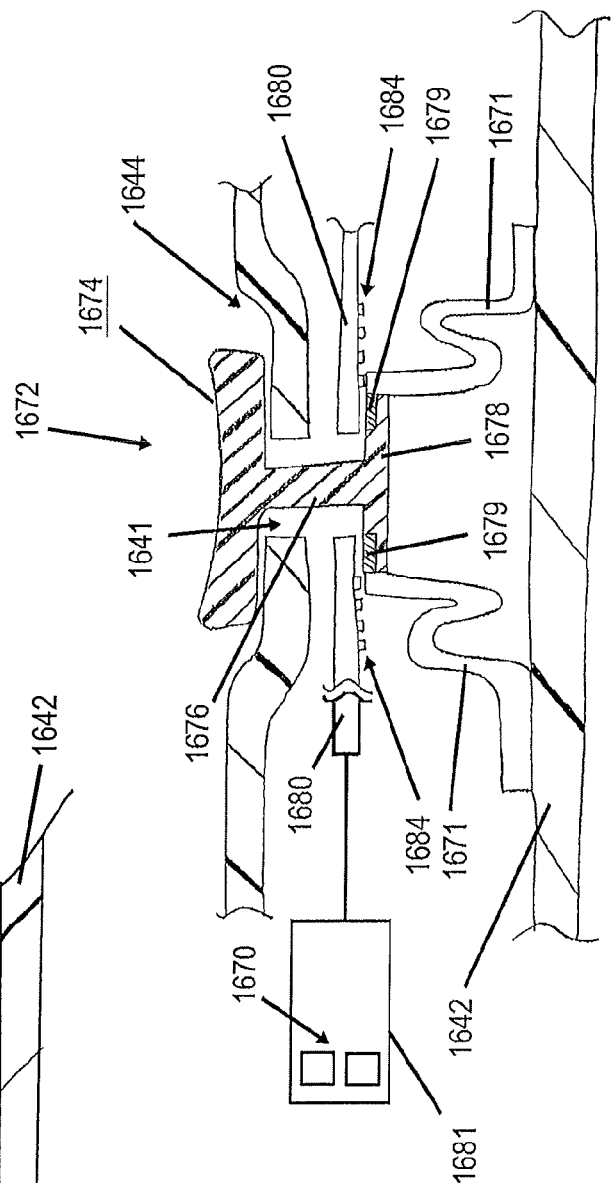
FIG. 13 depicts a partial side view of control and activation components of the device of FIG. 11, shown with the handle housing and button assembly in cross section.
Figure 14:
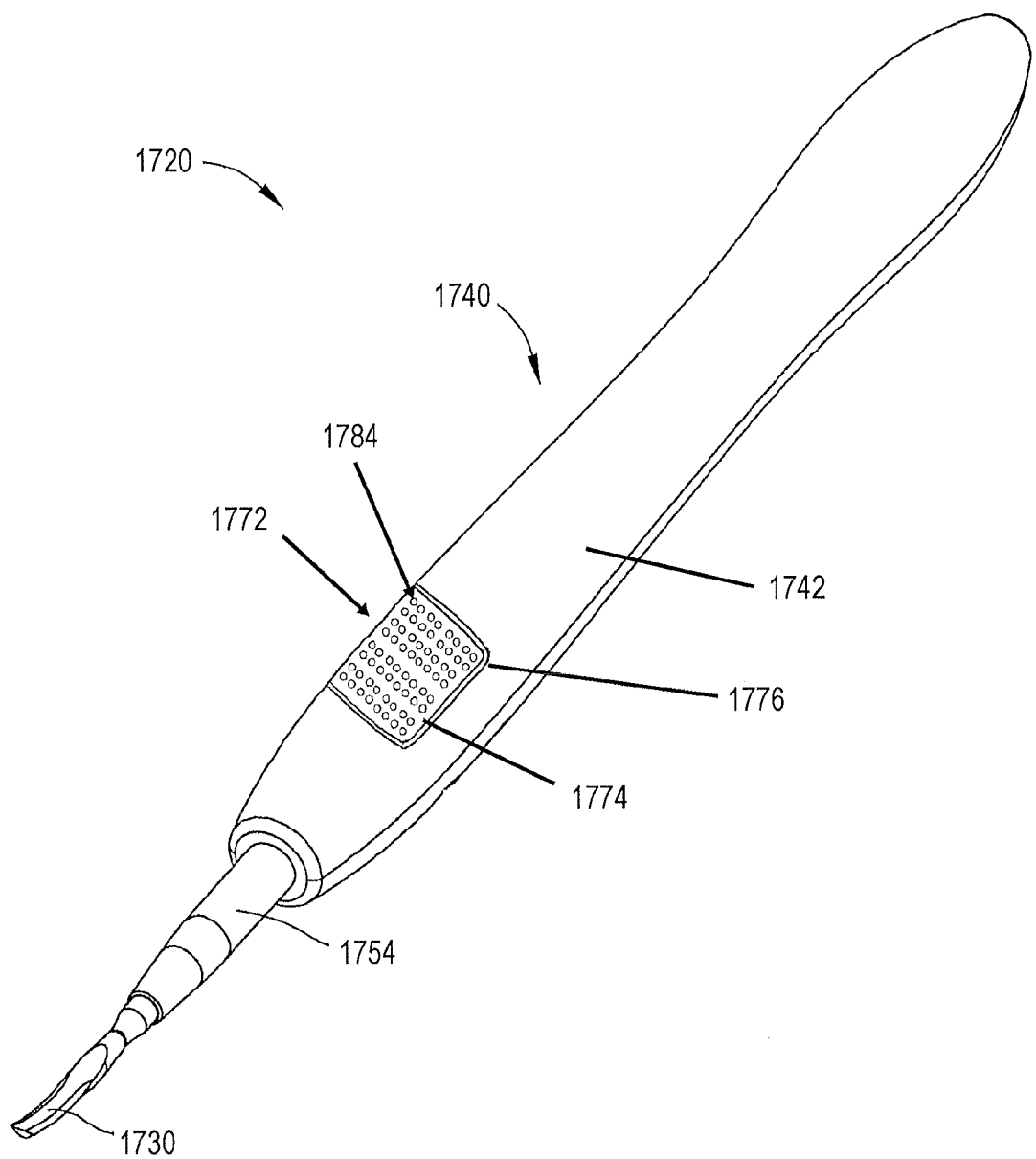
FIG. 14 depicts a perspective view of another exemplary surgical device.
Figure 15:
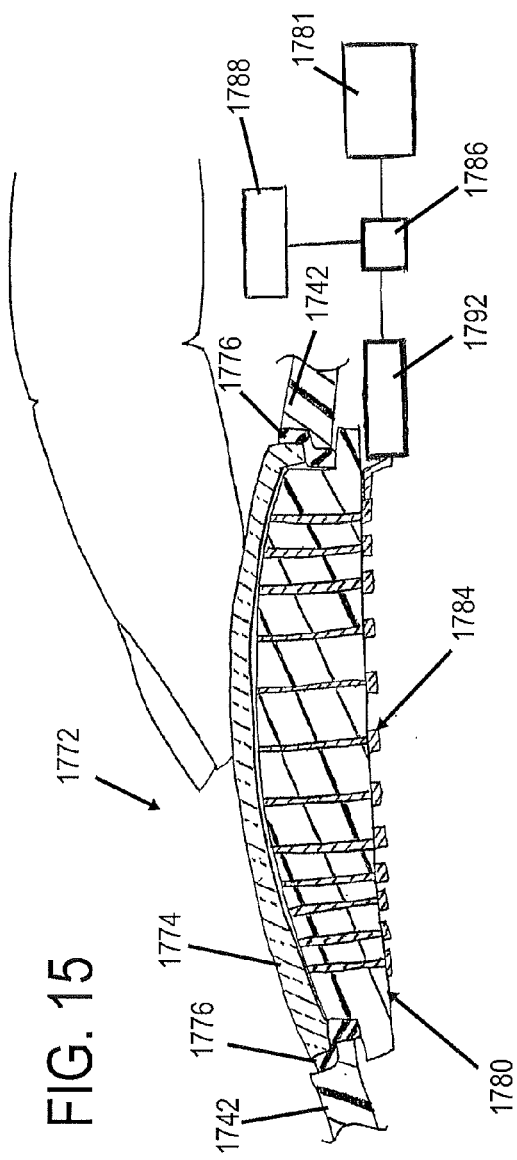
FIG. 15 depicts a partial side cross-sectional view of exemplary activation components for the exemplary surgical device of FIG. 14.

As noted above, housing shell (850) and control member (852) are rotatable relative to each other in the present example. As also noted above, control member (852) and blade (830) rotate unitarily with each other in the present example. Therefore, it should be understood that the user may rotate blade (830) relative to housing shell (850) by rotating control member (852) relative to housing shell (850). For instance, the user may use his or her or finger to rotate control member (852) while gripping housing shell (850) with the rest of his or her hand. Housing shell (850) may thus provide a mechanical ground during use of instrument (820), with control member (852) being used to rotate blade (830) to a selected rotational orientation relative to this ground (in addition to control member (852) being used to select a level of ultrasonic energy to be applied to blade (830)). As also noted above, tail section (860) is rotatable relative to both housing shell (850) and control member (852). Furthermore, as shown in FIGS. 13-15, cable (814) extends downwardly from tail section (860). Thus, this rotatability of tail section (860) and the downward orientation of cable (814) may help prevent cable (814) from getting twisted and/or in the way of the user. That is, the rotatability of tail section (860) may help to maintain the downward orientation of cable (814), despite the user's rotation of housing shell (850) and/or control member (852) during use of instrument (820). Furthermore, the use of slip rings (and/or other types of components) may prevent the electrical connections from the ultrasonic transducer (and/or other components) to cable (814) from restricting the degree to which housing shell (850) and/or control member (852) relative to tail section (860).

Handpiece (840) of the present example may be gripped by the user in a variety of ways. By way of example only, a user may grip handpiece (840) like a pencil, with a single hand, with handpiece (840) resting in the crook of the user's hand between the user's thumb and index finger. As another merely illustrative example, the user may grip handpiece (840) with their palm around handpiece (840). It should also be understood that, as noted above, the configuration and rotatability of control member (852) may permit the user to re-orient blade (730) to a selected rotational orientation, while still allowing external surface (853) to be reached and manipulated with relative ease. Of course, any suitable gripping technique may be used.

IV. Exemplary Ultrasonic Surgical Instrument with Control and Activation Strip FIG. 8 depicts another exemplary ultrasonic surgical instrument (920), comprising a blade (930) positioned distally relative to a handpiece (940). An ultrasonic transducer (not shown) is secured in handpiece (940), and may be coupled with an ultrasonic generator (not shown) in accordance with the teachings herein. An ultrasonic waveguide (not shown) is positioned within a sheath (932), which extends distally from handpiece (940). The ultrasonic waveguide couples the ultrasonic transducer with blade (930) in accordance with the teachings herein. It should therefore be understood that an ultrasonic generator may be used to activate the ultrasonic transducer of handpiece (940), and that the activated ultrasonic transducer may transmit ultrasonic vibration to blade (930) via the ultrasonic waveguide in accordance with the teachings herein. Handpiece (940) may be configured to substantially isolate the hand of the user relative to these ultrasonic vibrations. It should also be understood that ultrasonically vibrating blade (930) may be used to perform a variety of surgical procedures. Various other components that may be incorporated into handpiece (940), including but not limited to various components and configurations of electric circuitry, will be apparent to those of ordinary skill in the art in view of the teachings herein.

Instrument (920) of the present example further comprises a control and activation strip (950). Control and activation strip (950) is operable to act as a switch selectively coupling the ultrasonic transducer with the ultrasonic generator. In particular, control and activation strip (950) is operable to simultaneously ultrasonically activate blade (930) and select a desired level of ultrasonic energy to be applied to blade (930). For instance, like control member (852) described above, control and activation strip (950) may control the level of ultrasonic energy applied to blade (930) based at least in part on the longitudinal position at which the user's finger or hand engages control and activation strip (950). For instance, a user touching the distal end of control and activation strip (950) (e.g., the end closest to blade (930)) may result in ultrasonic activation of blade (930) at a "maximum" level of ultrasonic energy; while a user touching the proximal end of control and activation strip (950) (e.g., the end farthest from blade (930)) may result in ultrasonic activation of blade (930) at a "minimum" level of ultrasonic energy.

In some other versions, control and activation strip (950) also provides selectability of ultrasonic energy levels between the "minimum" and "maximum" level, such as when the user touches the longitudinally middle region of control and activation strip (950). In some such versions, the available energy levels are discrete and predetermined. For instance, as the user moves their hand or finger longitudinally along control and activation strip (950), from the distal end of control and activation strip (950) toward the proximal end of control and activation strip (950), the ultrasonic energy level may start at the "maximum" level and decrease in stepped increments in accordance with the longitudinal position of the user's hand or finger on control and activation strip (950). Discrete energy levels may thus be associated with discrete longitudinal ranges of length along control and activation strip (950).

In some other versions, the available ultrasonic energy levels may be virtually infinitely variable within a predetermined range. For instance, the ultrasonic energy level may be a substantially linear function of the longitudinal position of the user's hand or finger along the length of control and activation strip (950), such that the ultrasonic energy level progressively and substantially continuously increases or decreases as the user's hand or finger is slid along control and activation strip (950).

Figure 8A:
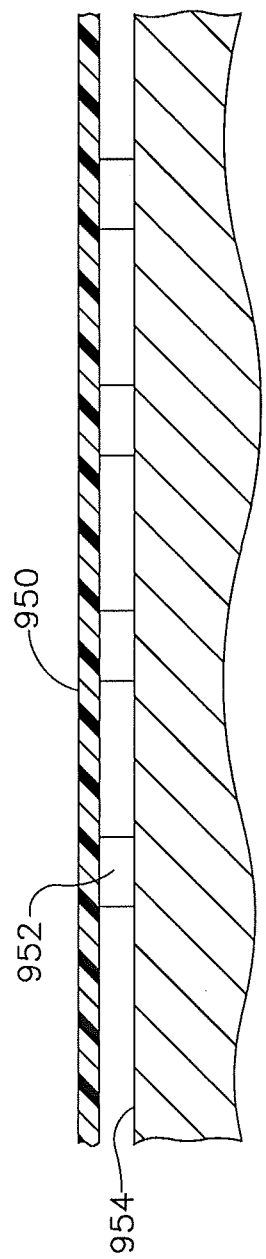
FIG. 8A depicts a partial side cross-sectional view of control and activation components of the ultrasonic surgical device of FIG. 8.

It should be understood that various types of technologies may be incorporated into control and activation strip (950) to allow it to sense and react to the longitudinal position at which the user's hand touches or presses control and activation strip (950). One merely illustrative example is shown in FIG. 8A. As shown, control and activation strip (950) is positioned over a plurality of button switches (952), which are mounted to a substrate (954). In this example, control and activation strip (950) comprises a flexible material (e.g., silicone, rubber, etc.). Button switches (952) may include capacitive switches, thin film switches, electromechanical buttons, or any other type of "button" described herein. Substrate (954) may comprise a printed circuit board having traces that are in communication with button switches (952) and other circuitry of instrument (920). Alternatively, substrate (954) may comprise any other suitable structure having any suitable properties.

In this example, button switches (952) are sized and spaced such that at least one button switch (952) will be actuated when a user presses his or her finger against control and activation strip (950), regardless of where the user presses his or her finger against control and activation strip (950). For instance, some versions of instrument (920) may include eight button switches (952) positioned equidistantly along the length of control and activation strip (950). Alternatively, any other suitable number of buttons switches (952) may be used, in any other suitable arrangement. With having such button switches (952) aligned along the length of control and activation strip (950), button switches (952) may be used to sense the longitudinal position of the user's finger along control and activation strip (950) and communicate with circuitry of instrument (920) accordingly. Various components and configurations of circuitry that may be in communication with button switches (952) will be apparent to those of ordinary skill in the art in view of the teachings herein. Of course, a linear array of button switches (952) is just one example. Similarly, other suitable ways in which the ultrasonic energy level of blade (930) may be based at least in part on the longitudinal position of the user's hand or finger along control and activation strip (950) will be apparent to those of ordinary skill in the art in view of the teachings herein. By way of example only, a variable resistor and/or some other type(s) of circuit component(s) may be responsive to the longitudinal position of the user's hand or finger along control and activation strip (950), and may provide a virtually infinitely variable level of electrical power (within a predefined range) to the ultrasonic transducer in the handpiece (940), which may thereby provide a virtually infinitely variable level of ultrasonic energy (within a predefined range) at blade (930).

In some alternative versions, control and activation strip (950) may comprise a plurality of capacitive switches; a plurality of resistive sensors; resonant cavity switching technology; infrared sensing technology; technology that uses a resonant, standing wave on a surface that is perturbed by the presence of a finger; and/or any other suitable type of technology. Still other suitable types of and arrangements of switches, sensors, or other technology that may be incorporated into control and activation strip (950) will be apparent to those of ordinary skill in the art in view of the teachings herein. Various ways in which such various types of control and activation strip (950) components may be incorporated into the circuitry of instrument (920), as well as various circuit components that may accompany or be coupled with variations of control and activation strip (950), will also be apparent to those of ordinary skill in the art in view of the teachings herein.

As noted above, activation and ultrasonic energy level selection are both provided through control and activation strip (950) in instrument (920) of the present example. For instance, instrument (920) may be configured such that as soon as a user touches control and activation strip (950), such touching may simultaneously effect selection of an ultrasonic energy level (e.g., in accordance with the longitudinal position at which control and activation strip (950) is touched) and activation of blade (930). As another merely illustrative example, instrument (920) may be configured such that the role of control and activation strip (950) as ultrasonic energy level selector or blade (930) activator is based at least in part on the way in which the user touches control and activation strip (950). For instance, the user may select an ultrasonic energy level by sliding their finger along control and activation strip (950) to a longitudinal position associated with a desired ultrasonic energy level; then activate blade (930) by tapping or double-tapping control and activation strip (950). As another non-limiting example, ultrasonic energy level selection may be based on a number of taps on control and activation strip (950) (e.g., more taps provides higher ultrasonic energy level); while activation of blade (930) is effected through touching control and activation strip (950) for at least a certain duration of time (e.g., three seconds). Alternatively, any other suitable combination of touching control and activation strip (950), sliding against control and activation strip (950), tapping against control and activation strip (950), etc., may be used to provide selection of an ultrasonic energy level and/or activation of blade (930). Such alternatives will be apparent to those of ordinary skill in the art in view of the teachings herein. Furthermore, a separate activation button may be provided to activate blade (930), in lieu of or in addition to providing activation of blade (930) via control and activation strip (950).

Handpiece (940) of the present example may be gripped by the user in a variety of ways. By way of example only, a user may grip handpiece (940) like a pencil, with a single hand, with handpiece (940) resting in the crook of the user's hand between the user's thumb and index finger. As another merely illustrative example, the user may grip handpiece (940) with their palm around handpiece (940). It should also be understood that the configuration of control and activation strip (950) may permit the user to rotate the entire handpiece (940) in the user's hand (e.g., about the longitudinal axis defined by handpiece (940)), such as to re-orient blade (930) to a selected rotational orientation, while still allowing control and activation strip (950) to be reached and manipulated with relative ease with handpiece (940) in different rotational orientations. For instance, in some gripping styles of handpiece (940), the user may access and manipulate activation strip (950) using their index finger, middle finger, or other finger. In addition or in the alternative, in some gripping styles of handpiece (940), the user may access and manipulate activation strip (950) using their thumb. Of course, any suitable gripping technique may be used. Furthermore, gripping techniques may be changed or adjusted during a given procedure.

V. Exemplary Ultrasonic Surgical Instrument with Angularly Arrayed Ribs

Figures 9, 10:
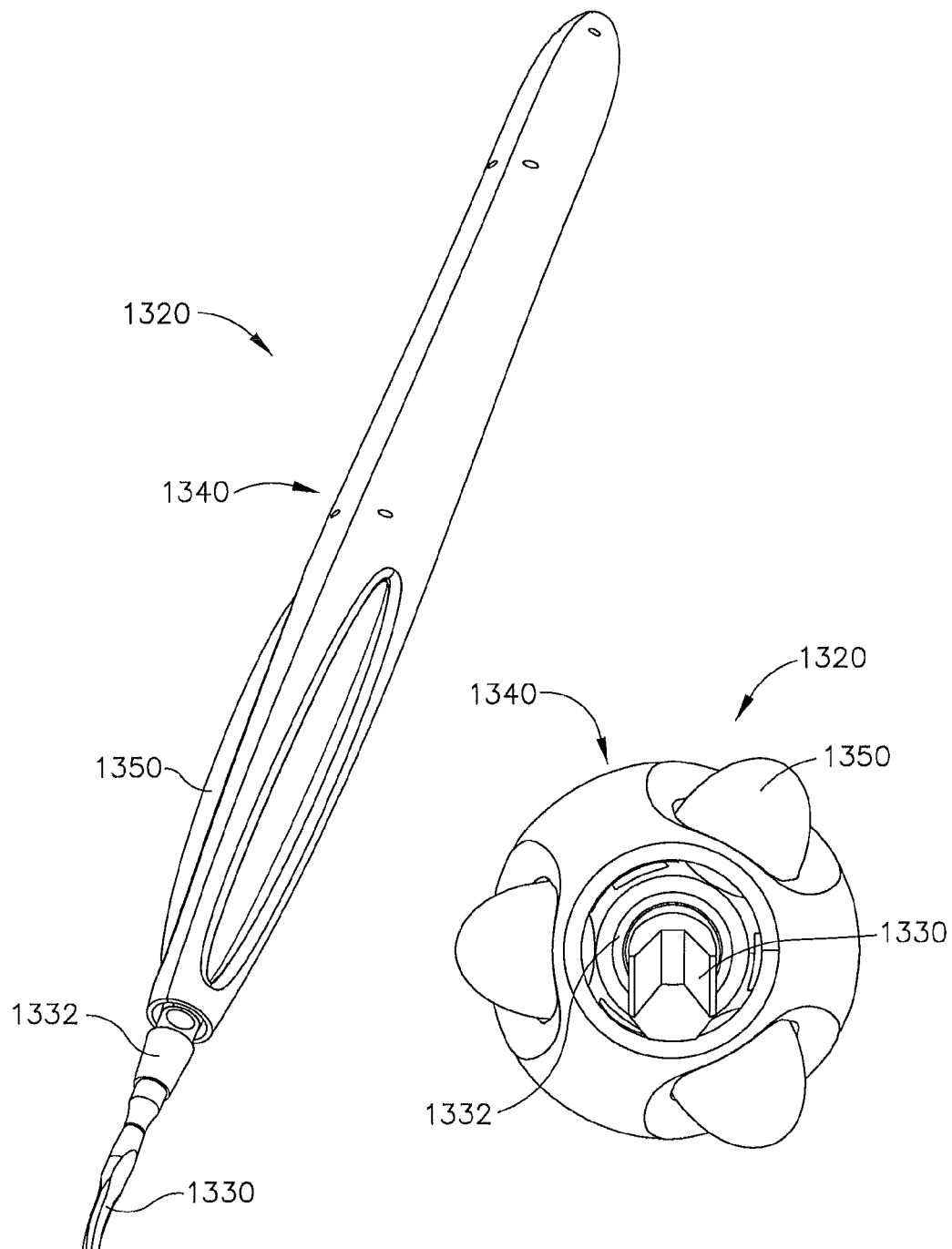
FIG. 9 depicts a perspective view of another exemplary ultrasonic surgical device, having a plurality of control and activation surfaces.
FIG. 10 depicts an end view of the ultrasonic surgical device of FIG. 9.

FIGS. 9-10 depict another exemplary ultrasonic surgical instrument (1320), comprising a blade (1330) positioned distally relative to a handpiece (1340). An ultrasonic transducer (not shown) is secured in handpiece (1340), and may be coupled with an ultrasonic generator (not shown) in accordance with the teachings herein. An ultrasonic waveguide (not shown) is positioned within a sheath (1332), which extends distally from handpiece (1340). The ultrasonic waveguide couples the ultrasonic transducer with blade (1330) in accordance with the teachings herein. It should therefore be understood that an ultrasonic generator may be used to activate the ultrasonic transducer of handpiece (1340), and that the activated ultrasonic transducer may transmit ultrasonic vibration to blade (1330) via the ultrasonic waveguide in accordance with the teachings herein. Handpiece (1340) may be configured to substantially isolate the hand of the user relative to these ultrasonic vibrations. It should also be understood that ultrasonically vibrating blade (1330) may be used to perform a variety of surgical procedures. Various other components that may be incorporated into handpiece (1340), including but not limited to various components and configurations of electric circuitry, will be apparent to those of ordinary skill in the art in view of the teachings herein.

Instrument (1320) of the present example further comprises a three control and activation ribs (1350). Control and activation ribs (1350) are angularly arrayed about the longitudinal axis defined by handpiece (1340) in increments of 120°. Of course, instrument (1320) may have any other suitable number of control and activation ribs (1350). Similarly, control and activation ribs (1350) may be provided in any other suitable arrangement, including but not limited to alternative angular arrays. Other suitable configurations and arrangements of control and activation ribs (1350) will be apparent to those of ordinary skill in the art in view of the teachings herein. The following description will refer to control and activation ribs (1350) in the singular form, it being understood that the description may apply to all control and activation ribs (1350) of instrument (1320).

Control and activation rib (1350) is operable to act as a switch selectively coupling the ultrasonic transducer with the ultrasonic generator. In particular, control and activation rib (1350) is operable to simultaneously ultrasonically activate blade (1330) and select a desired level of ultrasonic energy to be applied to blade (1330). For instance, as with control and activation strip (950) described above, control and activation rib (1350) may control the level of ultrasonic energy applied to blade (1330) based at least in part on the longitudinal position at which the user's finger or hand engages control and activation rib (1350). Indeed, any or all of the teachings above with respect to activation strip (950) (including but not limited to features, operability, variations, etc.) may be readily applied to each activation rib (1350). Still other suitable types of and arrangements of switches, sensors, or other technology that may be incorporated into control and activation rib (1350) will be apparent to those of ordinary skill in the art in view of the teachings herein. Various ways in which such various types of control and activation rib (1350) components may be incorporated into the circuitry of instrument (1320), as well as various circuit components that may accompany or be coupled with variations of control and activation rib (1350), will also be apparent to those of ordinary skill in the art in view of the teachings herein.

In some versions, the user must actuate at least two control and activation ribs (1350) simultaneously in order to activate blade (1330). Alternatively, any other suitable method or combination of touching control and activation rib (1350), sliding against control and activation rib (1350), tapping against control and activation rib (1350), etc., may be used to provide selection of an ultrasonic energy level and/or activation of blade (1330). Such alternatives will be apparent to those of ordinary skill in the art in view of the teachings herein. Furthermore, a separate activation button may be provided to activate blade (1330), in lieu of or in addition to providing activation of blade (1330) via control and activation rib (1350).

Handpiece (1340) of the present example may be gripped by the user in a variety of ways. By way of example only, a user may grip handpiece (1340) like a pencil, with a single hand, with handpiece (1340) resting in the crook of the user's hand between the user's thumb and index finger. As another merely illustrative example, the user may grip handpiece (1340) with their palm around handpiece (1340). It should also be understood that the configuration and arrangement of control and activation ribs (1350) may permit the user to rotate the entire handpiece (1340) in the user's hand (e.g., about the longitudinal axis defined by handpiece (1340)), such as to re-orient blade (1330) to a selected rotational orientation, while still allowing at least one control and activation rib (1350) to be reached and manipulated with relative ease with handpiece (1340) in different rotational orientations. Of course, any suitable gripping technique may be used.

Figure 11:
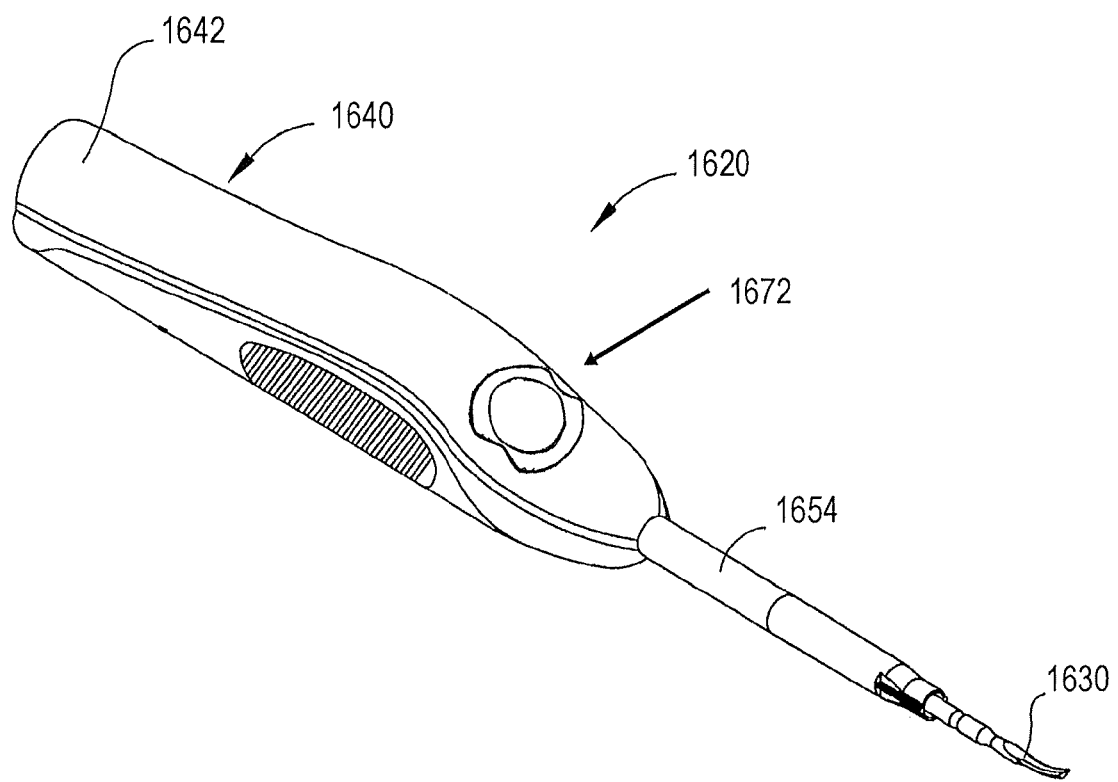
FIG. 11 depicts a perspective view of another exemplary surgical device.
Figure 12:
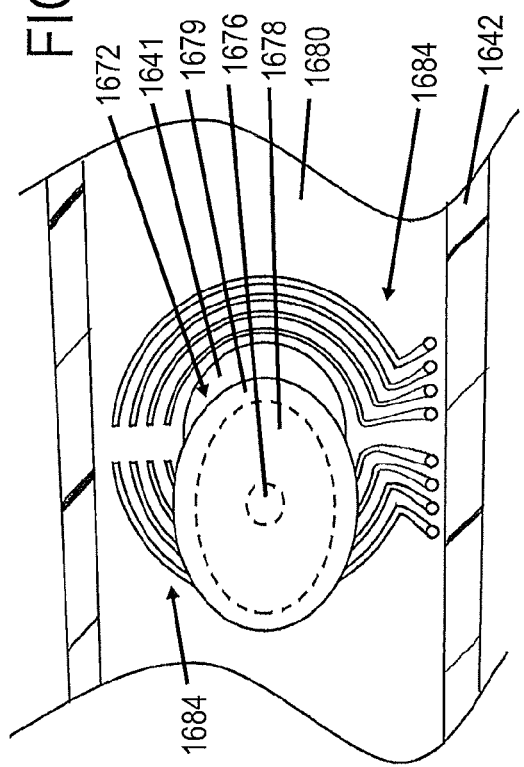
FIG. 12 depicts a partial bottom view of control and activation components of the device of FIG. 11, shown with the handle housing in cross section.

VI. Exemplary Surgical Instrument with Floating Button for Combined Activation and Control FIGS. 11-13 depict another exemplary surgical instrument (1620), comprising a blade (1630) positioned distally relative to a handpiece (1640). In the present example, surgical instrument (1620) is an ultrasonic surgical instrument and the discussion above with respect to FIGS. 1-4 generally applies to surgical instrument (1620), with certain differences discussed below. In some other versions, surgical instrument (1620) is an RF electrosurgical surgical instrument. Still in other versions, surgical instrument (1620) can be another type of powered surgical instrument that can be activated and controlled using a floating button design as described below. In view of the teachings herein, various ways to adapt a floating button design for activation and control of various types of powered surgical instruments will be apparent to those of ordinary skill in the art.

In the present example, an ultrasonic transducer (not shown) is secured in handpiece (1640), and may be coupled with an ultrasonic generator (not shown) in accordance with the teachings herein. An ultrasonic waveguide (not shown) is positioned within a sheath (1654), which extends distally from handpiece (1640). The ultrasonic waveguide couples the ultrasonic transducer with blade (1630) in accordance with the teachings herein. It should therefore be understood that an ultrasonic generator may be used to activate the ultrasonic transducer of handpiece (1640), and that the activated ultrasonic transducer may transmit ultrasonic vibration to blade (1630) via the ultrasonic waveguide in accordance with the teachings herein. Handpiece (1640) may be configured to substantially isolate the hand of the user relative to these ultrasonic vibrations. It should also be understood that ultrasonically vibrating blade (1630) may be used to perform a variety of surgical procedures. Various other components that may be incorporated into handpiece (1640), including but not limited to various components and configurations of electric circuitry, will be apparent to those of ordinary skill in the art in view of the teachings herein.

Instrument (1620) of the present example further comprises a floating button (1672) for control and activation. Floating button (1672) is operable to act as a switch selectively coupling the ultrasonic transducer with the ultrasonic generator. In particular, floating button (1672) is operable to simultaneously ultrasonically activate blade (1630) and select a desired level of ultrasonic energy to be applied to blade (1630). For instance, floating button (1672) may activate ultrasonic energy that is applied to blade (1630) based at least in part on the presence of longitudinal displacement of floating button (1672) from a center point or home position, due to a user's finger pushing or pulling on floating button (1672). Furthermore, floating button (1672) may control the level of ultrasonic energy applied to blade (1630) based at least in part on the amount of the longitudinal displacement of floating button (1672).

In the present example, handpiece (1640) comprises housing (1642). Housing (1642) comprises an opening (1641) for receiving a portion of floating button (1672). Housing (1642) also comprises a recessed portion (1644) surrounding opening (1641). Floating button (1672) is positioned within recessed portion (1644) of housing (1642) and the nature of this configuration can provide a user with a tactile reference point for accessing and controlling surgical instrument (1620) without needing to visually sight floating button (1672).

Positioned within housing (1642) is circuit board (1680). Circuit board (1680) comprises proximity circuit (1681) having an array of metal contacts (1684) in the form of half rings surrounding the perimeter of floating button (1672). Circuit (1681) includes one or more proximity switches (1670) for activating blade (1630) and controlling the amount of ultrasonic energy directed to blade (1630). In some versions, the description of exemplary circuit (40) as described and shown in FIG. 2 generally applies to circuit (1681). Of course other exemplary circuit architecture can be used for circuit (1681) and such other exemplary circuit architecture will be apparent to those of ordinary skill in the art in view of the teachings herein. In the present example circuit board (1680) is connected with control circuitry (16) of ultrasonic generator (12). When one or more of proximity switches (1670) are activated, a signal is sent to control circuitry (16) and ultrasonic generator (12) is activated to generate the energy that in turn is provided to the ultrasonic transducer of surgical instrument (1620), and ultimately to blade (1630).

Floating button (1672) of surgical instrument (1620) comprises concave surface (1674) that serves as the placement area for a user's finger. Button (1672) comprises post (1676) that extends through opening (1641) in housing (1642) of handpiece (1640). Button (1672) further comprises base (1678) and metallic ring (1679). In the present example, metallic ring (1679) is inlaid in base (1678) of button (1672) and surrounds post (1676). On each side of base (1678) of button (1672) are springs (1671). In some versions, springs (1671) are comprised of polymeric material and/or as a molded elastomer, e.g., including silicones or thermoplastic elastomers like Kraton, though other suitable materials and configurations for springs (1671) will be apparent to those of ordinary skill in the art in view of the teachings herein. Springs (1671) connect with housing (1642) and are configured to compress as button (1672) is moved longitudinally forward or backward relative to a home position. When the user stops pushing or pulling button (1672), springs (1671) are biased such that button (1672) returns to the home position. The home position for button (1672) is shown in FIG. 13, and is the position where springs (1671) are in their uncompressed states and metallic ring (1679) is not in contact with metal contacts (1684) of proximity circuit (1681). In the home position, none of proximity switches (1671) are activated and surgical instrument (1620) is in a deactivated state.

As shown in the illustrated version, the configuration of floating button (1672) and the ring shapes for proximity circuit (1681) and metallic ring (1679) allow a user some degree of lateral movement of button (1672) when using surgical instrument (1620). Accordingly, surgical instrument (1620) can be activated by movement of button (1672) in the general forward or backward direction relative to the longitudinal axis of handpiece (1640). This feature can allow the user to active instrument (1620) as they change positions of instrument (1620) relative to their grip. In some versions, instrument (1620) can be activated when button (1672) is moved anywhere in the forward or backward pie-shaped regions defined by about 135 degrees on each side of the longitudinal axis defined by handpiece (1640). By way of example only, in some versions these pie-shaped regions can be marked on handpiece (1640) and/or handpiece (1640) can have pie-shaped recessed regions to indicate this mobility range of button (1672). It should therefore be understood that button (1672) may be moved along axes that are oblique relative to the longitudinal axis defined by handpiece (1640) and sheath (1654), while still activating blade (1630).

In use, a user can grasp instrument (1620) like a pencil, placing their index finger on floating button (1672) and feeling concave surface (1674). The user positions blade (1630) against the tissue, and the user slightly presses their finger in a generalized forward or backward motion which moves floating button (1672) and metallic ring (1679) over one or more of proximity switches (1670) thereby activating and providing power to blade (1630). As the user completes their task and removes their finger from floating button (1672), springs (1671) return button (1672) to the neutral or home position. This action moves metallic ring (1679) away from metal contacts (1684) thereby deactivating instrument (1620).

In some versions, the spacing of metal contacts (1684) and the associated proximity switches (1670) are configured such that as metallic ring (1679) moves over a metal contact (1684) that is located further from the home position of button (1672), more power is generated and directed to blade (1630). In some such versions, the available energy levels are discrete and predetermined. For instance, as the user moves button (1672) longitudinally forward or backward the ultrasonic energy level may start at the "minimum" level and increase in stepped increments as the position of button (1672) is moved further away from the home position. Discrete energy levels may thus be associated with discrete ranges of displacement of button (1672) from the home position. In some other versions, the available ultrasonic energy levels may be virtually infinitely variable within a predetermined range. For instance, the ultrasonic energy level may be a substantially linear function of the displacement of button (1672) from the home position, such that the ultrasonic energy level progressively and substantially continuously increases or decreases as the user moves button (1672) further from, or back toward, the home position.

In some versions, instrument (1620) is configured such that the movement of button (1672) in a forward direction provides a different energy response to blade (1630) compared to the same movement of button (1672) in the backward direction. By way of example only, and not limitation, instrument (1620) can be configured such that the forward movement operates instrument (1620) in one energy level range, and backward movement operates instrument (1620) in a different energy range. For example, moving button (1672) forward may operate instrument (1620) in a "high" energy level range, while moving button (1672) backward may operate instrument (1620) in a "low" energy range. Based on the teachings herein, other suitable configurations for the energy response to button (1672) displacement direction and amount will be apparent to those of ordinary skill in the art.

While the illustrated version in FIGS. 11-13 depict floating button (1672) as a component of the activation and control mechanism for instrument (1620), other suitable ways in which the ultrasonic energy level of blade (1630) may be based at least in part on the displacement of button (1672) or some other structure from a neutral or home position will be apparent to those of ordinary skill in the art in view of the teachings herein. By way of example only, some versions can use a variable resistor and/or some other type(s) of circuit component(s) responsive to the displacement of button (1672) or some other structure from a neutral or home position, and may provide a virtually infinitely variable level of electrical power (within a predefined range) to the ultrasonic transducer in the handpiece (1640), which may thereby provide a virtually infinitely variable level of ultrasonic energy (within a predefined range) at blade (1630). In some alternative versions, in place of button (1672), a plurality of capacitive switches, a plurality of resistive sensors, resonant cavity switching technology, infrared sensing technology, technology that uses a resonant standing wave on a surface that is perturbed by the presence of a finger, and/or any other suitable type of technology can be used. Still other suitable types of and arrangements of switches, sensors, or other technology that may be incorporated into instrument (1620) will be apparent to those of ordinary skill in the art in view of the teachings herein. Various ways in which such various types activation and control components may be incorporated into the circuitry of instrument (1620), as well as various circuit components that may accompany or be coupled with variations of activation and control components, will also be apparent to those of ordinary skill in the art in view of the teachings herein.

While handpiece (1640) of instrument (1620) has been described as being held by a user in a pencil grip fashion, with handpiece (1640) resting in the crook of the user's hand between the user's thumb and index finger, handpiece (1640) of the present example may be gripped by the user in any variety of ways. By way of further example only, a user may grip handpiece (1640) with their palm around handpiece (1640) and thumb on button (1672). It should also be understood that the configuration of activation and control components of instrument (1620) may permit the user to rotate the entire handpiece (1640) in the user's hand such as to re-orient blade (1630) to a selected rotational orientation, while still allowing floating button (1672) to be reached and manipulated with relative ease with handpiece (1640) in different rotational orientations. For instance, in some gripping styles of handpiece (1640), the user may access and manipulate floating button (1672) using their index finger, middle finger, or other finger. In addition or in the alternative, in some gripping styles of handpiece (1640), the user may access and manipulate floating button (1672) using their thumb. Of course, any suitable gripping technique may be used. Furthermore, gripping techniques may be changed or adjusted during a given procedure.

VII. Exemplary Surgical Instrument with Sealed Activation and Control

FIGS. 14-17 depict another exemplary surgical instrument (1720) comprising a blade (1730) positioned distally relative to a handpiece (1740), and having a sealed activation and control assembly. In the present example, surgical instrument (1720) is an ultrasonic surgical instrument and the discussion above with respect to FIGS. 1-4 generally applies to surgical instrument (1720), with certain differences discussed below. In some other versions, surgical instrument (1720) is an RF electrosurgical surgical instrument. Still in other versions, surgical instrument (1720) can be another type of powered surgical instrument that can be activated and controlled using a sealed activation and control assembly as described below. In view of the teachings herein, various ways to adapt a sealed activation and control assembly design for activation and control of various types of powered surgical instruments will be apparent to those of ordinary skill in the art.

In the present example, an ultrasonic transducer (not shown) is secured in handpiece (1740), and may be coupled with an ultrasonic generator (not shown) in accordance with the teachings herein. An ultrasonic waveguide (not shown) is positioned within a sheath (1754), which extends distally from handpiece (1740). The ultrasonic waveguide couples the ultrasonic transducer with blade (1730) in accordance with the teachings herein. It should therefore be understood that an ultrasonic generator may be used to activate the ultrasonic transducer of handpiece (1740), and that the activated ultrasonic transducer may transmit ultrasonic vibration to blade (1730) via the ultrasonic waveguide in accordance with the teachings herein. Handpiece (1740) may be configured to substantially isolate the hand of the user relative to these ultrasonic vibrations. It should also be understood that ultrasonically vibrating blade (1730) may be used to perform a variety of surgical procedures. Various other components that may be incorporated into handpiece (1740), including but not limited to various components and configurations of electric circuitry, will be apparent to those of ordinary skill in the art in view of the teachings herein.

Figure 16:
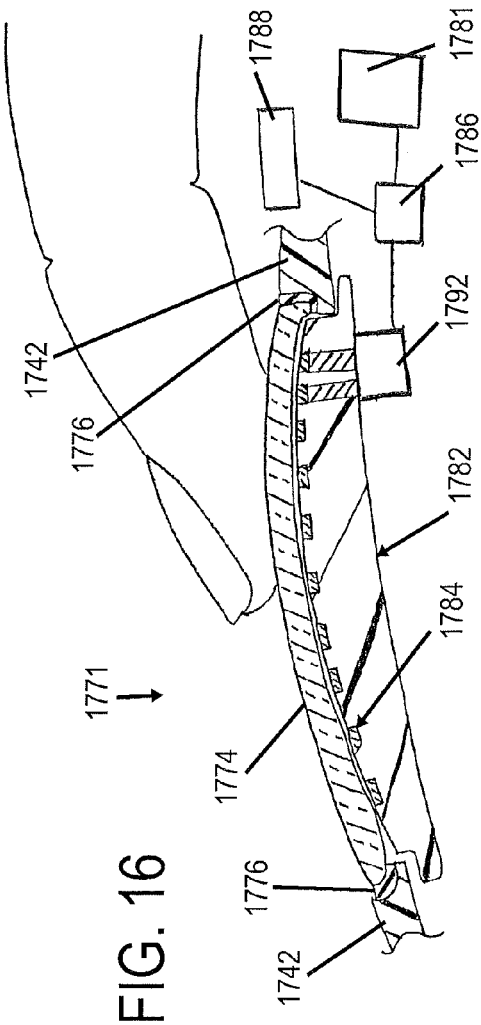
FIG. 16 depicts a partial side cross-sectional view of another version of exemplary activation components for the exemplary surgical device of FIG. 14.

In the present example, instrument (1720) comprises one of the versions of exemplary activation and control assemblies (1771, 1772) as shown in FIGS. 15 and 16, where the electrical components are sealed within handpiece (1740) to allow handpiece (1740) to undergo steam sterilization without causing any damage to such electrical components. Activation and control assembly (1771) is generally similar to activation and control assembly (1772), a difference being the precise configuration of molded interconnect devices (1780, 1782). As will be described in greater detail below, both activation and control assemblies (1771, 1772) use expected finger contact patterns to recognize the presence of the finger to activate and control instrument (1720). By way of non-limiting example, in one version, activation and control assembly (1771, 1772) uses a matrix of pins (1784) that are either on or off, and provides a digitized impression of the finger on a contact surface (1774). By way of a further non-limiting example, in another version, activation and control assembly (1771, 1772) uses a variable voltage at each pin (1784) that corresponds to the effective change in capacitance as the finger contacts a contact surface (1774) above each pin location. The resulting voltage pattern or map can be correlated to the expected patterns or maps to confirm the presence of a finger. The following paragraphs in this section will focus on activation control assembly (1772), it being understood that the teachings apply equally to activation and control assembly (1771).

Activation and control assembly (1772) is operable to act as a switch selectively coupling the ultrasonic transducer with the ultrasonic generator. In particular, activation and control assembly (1772) is operable to simultaneously ultrasonically activate blade (1730) and select a desired level of ultrasonic energy to be applied to blade (1730). For instance, like control and activation strip (950) described above, activation and control assembly (1772) may control the level of ultrasonic energy applied to blade (1730) based at least in part on the longitudinal position at which the user's finger or hand engages activation and control assembly (1772). For instance, a user touching the distal end of activation and control assembly (1772) (e.g., the end closest to blade (1730)) may result in ultrasonic activation of blade (1730) at a "maximum" level of ultrasonic energy; while a user touching the proximal end of activation and control assembly (1772) (e.g., the end farthest from blade (1730)) may result in ultrasonic activation of blade (1730) at a "minimum" level of ultrasonic energy.

In some other versions, activation and control assembly (1772) also provides selectability of ultrasonic energy levels between the "minimum" and "maximum" level, such as when the user touches the longitudinally middle region of activation and control assembly (1772). In some such versions, the available energy levels are discrete and predetermined. For instance, as the user moves their hand or finger longitudinally along activation and control assembly (1772), from the distal end of activation and control assembly (1772) toward the proximal end of activation and control assembly (1772), the ultrasonic energy level may start at the "maximum" level and decrease in stepped increments in accordance with the longitudinal position of the user's hand or finger on activation and control assembly (1772). Discrete energy levels may thus be associated with discrete longitudinal ranges of length along activation and control assembly (1772). In some other versions, the available ultrasonic energy levels may be virtually infinitely variable within a predetermined range. For instance, the ultrasonic energy level may be a substantially linear function of the longitudinal position of the user's hand or finger along the length of activation and control assembly (1772), such that the ultrasonic energy level progressively and substantially continuously increases or decreases as the user's hand or finger is slid along activation and control assembly (1772).

It should be understood that various types of technologies may be incorporated into activation and control assembly (1772) to allow it to be a sealed unit while sensing and reacting to the longitudinal position at which the user's hand touches or presses activation and control assembly (1772). Some merely illustrative examples are shown in FIGS. 14-17. As shown, activation and control assembly (1772) comprises contact surface (1774), seal (1776), and molded interconnect device (MID) (1780). In relation to FIGS. 1 and 2 presented above, in some versions MID (1780) is similar to all or a portion of printed circuit board (34), with the associated circuitry similar to all or a portion of circuit (40). Contact surface (1774) is located on the surface of housing (1742) and seal (1776) is placed between contact surface (1774) and housing (1742) such that the combined structure is airtight and watertight. In the present example, seal (1776) is an epoxy-based seal, though other types of seals may be suitable for use and such other types of seals will be apparent to those of ordinary skill in the art in view of the teachings herein. Contact surface (1774) is comprised of a non-permeable, radio wave transparent material. In the present example, contact surface (1774) is comprised of molded glass, though other types of materials, e.g., ceramic, etc. for contact surface (1774) may be suitable for use and such other materials will be apparent to those of ordinary skill in the art in view of the teachings herein. Although not required in all versions, in the present example, contact surface (1774) is configured to have a consistent thickness between the area a user will touch and the internal sensing surface or MID (1780).

MID (1780) comprises metal pins (1784) that attach with connector (1792). Connector (1792) attaches MID (1780) with at least one microprocessor (1786) and proximity circuit (1781), which powers MID (1780) in the present example. In relation to FIGS. 1 and 2 presented above, in some versions microprocessor (1786) comprises a component of a circuit, e.g., circuit (40), associated with a printed circuit board, e.g., circuit board (34). Metal pins (1784) are placed a fixed distance behind contact surface (1774) within handpiece (1740). Microprocessor (1786) acts as a switch between each pin (1784) and proximity circuit (1781). For example, upon activation, microprocessor (1786) detects voltage changes sensed at each pin (1784) attributed to contact with contact surface (1774) above the particular pin (1784) location, e.g., by a user's finger. In some versions, small changes in contact surface (1774) due to finger contact result in a change in the distance between contact surface (1774) and at least one of the pins (1784). This causes a change in the local capacitance and is measured as a voltage. It should be understood that the distance between contact surface (1774) and at least one of the pins (1784) may change due to deformation of contact surface (1774) and/or seal (1776) in response to a force exerted by the user's finger against contact surface (1774)

Microprocessor (1786) uses on-board volatile memory for mapping detected voltage changes. For instance, based on the detected voltage changes, microprocessor (1786) sends a signal to proximity circuit (1781). Proximity circuit (1781) reads the signal information for the particular pin (1784) and sends a signal containing the result back to microprocessor (1786). By way of example only, and not limitation, the signal sent from microprocessor (1786) to proximity circuit (1781) may indicate either the presence or absence of a voltage change at a particular pin (1784). In some versions, this signal may include an amount of voltage change detected. The result signal then sent from proximity circuit (1781) back to microprocessor (1786) may indicate the particular pin (1784) represents a closed switch or an open switch. By developing a map of the array of pins (1784) based on the result signal from proximity circuit (1781), comparisons can be made by microprocessor (1786) between maps for expected finger activations and maps for unexpected activations. Where a developed map from the detection process matches a known map for an expected finger activation, microprocessor (1786) signals to activate harmonic circuit (1788), which then causes a power source to produce and deliver ultrasonic energy to ultrasonic transducer to ultimately activate blade (1730). In relation to FIGS. 1 and 2 presented above, in some versions harmonic circuit (1788) is the same or similar to control circuitry (16) of generator (12). Where a developed map does not match a known map for an expected finger activation, microprocessor (1786) ignores the result signal from proximity circuit (1781) and the monitoring and mapping process repeats. This may substantially prevent inadvertent activation of blade (1730) that might otherwise be caused by incidental/inadvertent contact with contact surface (1774) (e.g. from a finger, fluids, setting instrument (1720) on a table or other surface, etc.).

Figure 17:
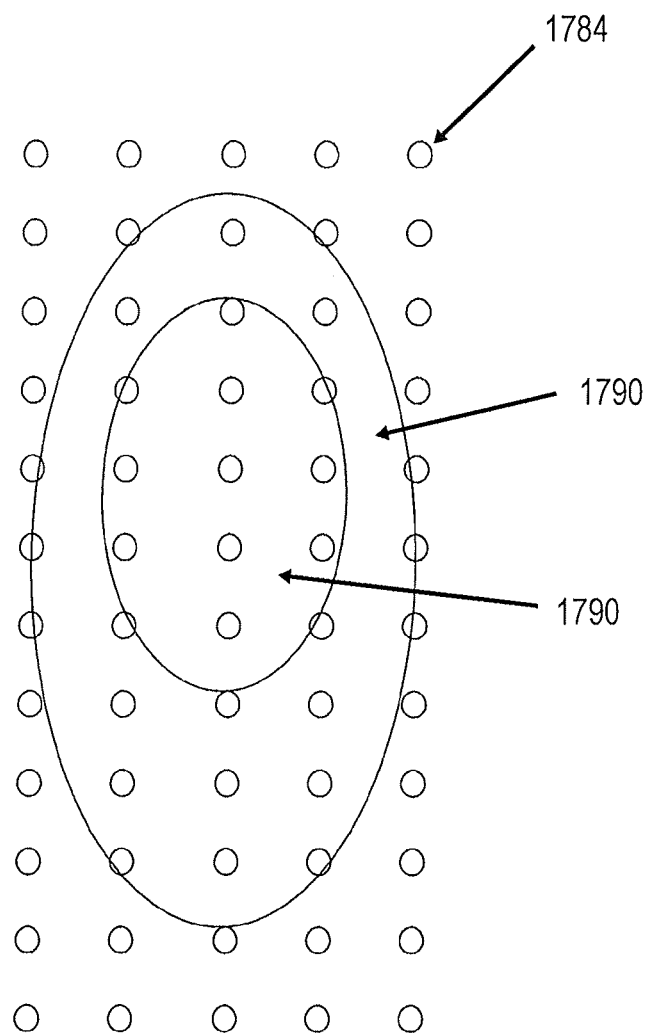
FIG. 17 depicts a partial top view of the exemplary activation components of FIGS. 15 and 16, showing the metal pins of a proximity circuit and exemplary first and second proximity regions.

In the present example, pins (1784) are sized and spaced such that at least one pin (1784) will be actuated when a user presses his or her finger against contact surface (1774), regardless of where the user presses his or her finger against contact surface (1774). For instance, some versions of instrument (1720) may include an array of pins (1784) positioned in a generally rectangular shape along the length of activation and control assembly (1772). In such an example, and as shown in FIG. 17, one or more regions (1790) can be defined based on, e.g., one or more generally oval shapes overlapping the array of rectangularly positioned pins (1784). Microprocessor (1786) and proximity circuit (1781) can be configured to recognize contact in the one or more regions (1790) and use the region information to develop more accurate and robust maps and map comparisons to known finger activation patterns. While the present example uses defined regions (1790) that encompass multiple pins (1784), instead or in addition to the concept of defined regions (1790) covering multiple pins (1784), as mentioned above, each pin (1784) can effectively be considered a single region for map development and comparison purposes. Furthermore, any suitable number of pins (1784) and regions (1790) may be used, in any suitable arrangement. By way of example only, in some versions pins (1784) are positioned around the entire circumference of handpiece (1740), such that a user can rotate instrument (1720) in their grip while activation and control assembly (1772) remain response to the user's finger contact. With having such pins (1784) and regions (1790) generally aligned along the length of activation and control assembly (1772), pins (1784) and regions (1790) may be used to sense the longitudinal position of the user's finger along activation and control assembly (1772) and communicate with circuitry of instrument (1720) accordingly as described above. Various components and configurations of circuitry that may be in communication with pins (1784) and regions (1790) will be apparent to those of ordinary skill in the art in view of the teachings herein.

Other suitable ways in which the ultrasonic energy level of blade (1730) may be based at least in part on the longitudinal position of the user's hand or finger along activation and control assembly (1772) will be apparent to those of ordinary skill in the art in view of the teachings herein. By way of example only, a variable resistor and/or some other type(s) of circuit component(s) may be responsive to the longitudinal position of the user's hand or finger along activation and control assembly (1772), and may provide a virtually infinitely variable level of electrical power (within a predefined range) to the ultrasonic transducer in the handpiece (1740), which may thereby provide a virtually infinitely variable level of ultrasonic energy (within a predefined range) at blade (1730). In some alternative versions, activation and control assembly (1772) may comprise a plurality of resistive sensors, resonant cavity switching technology, infrared sensing technology, technology that uses a resonant standing wave on a surface that is perturbed by the presence of a finger, and/or any other suitable type of technology. Still other suitable types of and arrangements of switches, sensors, or other technology that may be incorporated into activation and control assembly (1772) will be apparent to those of ordinary skill in the art in view of the teachings herein. Various ways in which such various types of components for activation and control assembly (1772) may be incorporated into the circuitry of instrument (1720), as well as various circuit components that may accompany or be coupled with variations of activation and control assembly (1772), will also be apparent to those of ordinary skill in the art in view of the teachings herein.

As noted above, activation and ultrasonic energy level selection are both provided through activation and control assembly (1772) in instrument (1720) of the present example. For instance, instrument (1720) may be configured such that as soon as a user touches activation and control assembly (1772), such touching may simultaneously effect selection of an ultrasonic energy level (e.g., in accordance with the longitudinal position at which activation and control assembly (1772) is touched) and activation of blade (1730). As another merely illustrative example, instrument (1720) may be configured such that the role of activation and control assembly (1772) as ultrasonic energy level selector or blade (1730) activator is based at least in part on the way in which the user touches activation and control assembly (1772). For instance, the user may select an ultrasonic energy level by sliding their finger along activation and control assembly (1772) to a longitudinal position associated with a desired ultrasonic energy level, then activate blade (1730) by tapping or double-tapping activation and control assembly (1772). As another non-limiting example, ultrasonic energy level selection may be based on a number of taps on activation and control assembly (1772) (e.g., more taps provides higher ultrasonic energy level); while activation of blade (1730) is effected through touching activation and control assembly (1772) for at least a certain duration of time (e.g., three seconds). Alternatively, any other suitable combination of touching activation and control assembly (1772), sliding against activation and control assembly (1772), tapping against activation and control assembly (1772), etc., may be used to provide selection of an ultrasonic energy level and/or activation of blade (1730). Such alternatives will be apparent to those of ordinary skill in the art in view of the teachings herein. Furthermore, a separate activation control may be provided to activate blade (1730), in lieu of or in addition to providing activation of blade (1730) via activation and control assembly (1772).

Handpiece (1740) of the present example may be gripped by the user in a variety of ways. By way of example only, a user may grip handpiece (1740) like a pencil, with a single hand, with handpiece (1740) resting in the crook of the user's hand between the user's thumb and index finger. As another merely illustrative example, the user may grip handpiece (1740) with their palm around handpiece (1740). It should also be understood that the configuration of activation and control assembly (1772) may permit the user to rotate the entire handpiece (1740) in the user's hand (e.g., about the longitudinal axis defined by handpiece (1740)), such as to re-orient blade (1730) to a selected rotational orientation, while still allowing activation and control assembly (1772) to be reached and manipulated with relative ease with handpiece (1740) in different rotational orientations. For instance, in some gripping styles of handpiece (1740), the user may access and manipulate activation and control assembly (1772) using their index finger, middle finger, or other finger. In addition or in the alternative, in some gripping styles of handpiece (1740), the user may access and manipulate activation and control assembly (1772) using their thumb. Of course, any suitable gripping technique may be used. Furthermore, gripping techniques may be changed or adjusted during a given procedure.

It should also be understood that, as referred to previously, the teachings herein are not limited to ultrasonic instruments. By way of example only, various teachings herein (including but not limited to instrument configuration, activation, energy selection, etc.) may be readily incorporated into RF surgical devices such as bi-polar or mono-polar devices, those used for cutting, coagulation, ablation, etc. Various ways in which teachings herein may be applied to RF surgical devices will be apparent to those of ordinary skill in the art. As another merely illustrative example, various teachings herein (including but not limited to instrument configuration, activation, energy selection, etc.) may be readily incorporated into surgical devices that have a mechanically actuated end effector (e.g., mechanically rotating tip, mechanically reciprocating tip, etc.). As yet another merely illustrative example, various teachings herein (including but not limited to instrument configuration, activation, energy selection, etc.) may be readily incorporated into surgical devices that use a laser or some other form of energy to perform a surgical function, therapeutic function, or some other type of function. Various other types of devices to which the teachings herein may be applied will be apparent to those of ordinary skill in the art.

It should be understood that any feature(s), component(s), configuration(s), and/or operability described herein with respect to one particular instrument (20, 120, 820, 920, 1320, 1620, 1720) or other example may readily be incorporated into any other instrument (20, 120, 820, 920, 1320, 1620, 1720) described herein. Therefore, none of the teachings herein should be understood as applying to only one particular version or embodiment of instrument (20, 120, 820, 920, 1320, 1620, 1720) described herein. Every teaching herein is contemplated as being interchangeable among versions and embodiments, such that every teaching herein may be applied to any instrument (20, 120, 820, 920, 1320, 1620, 1720) described herein, in any suitable fashion. By way of non-limiting example, pins (1784) of instrument (1720) may be aligned in just a single row or in just a single column. For instance, the button switches (952) in the control and activation strip (950) of the version shown in FIGS. 8-8A may be substituted with pins (1784). Also, each control and activation rib (1350) in the version shown in FIGS. 9-10 could have a line of pins (1784) underneath. Other various ways in which the teachings herein may be interchanged among various versions, examples, and embodiments will be apparent to those of ordinary skill in the art in view of the teachings herein.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. A powered surgical instrument comprising:
(a) a handpiece having a distal and proximal end;
(b) a housing defining an outer perimeter of the handpiece, wherein the housing comprises an opening;
(c) an end effector coupled with the handpiece, wherein the end effector is positioned distally relative to the distal end of the handpiece; and
(d) an input device associated with the handpiece, wherein the input device comprises a button, wherein the button further comprises:
(i) a first surface positioned outside the housing of the handpiece, wherein the first surface is configured for receiving a user's finger,
(ii) a post extending from the first surface through the opening of the housing, and

(iii) a base connected with the post and positioned within the housing;

wherein the input device is configured to activate the end effector and control an energy level provided to the end effector based on a radial displacement of the button from a neutral position, wherein the end effector is configured to provide selectively variable energy levels corresponding to radial displacement distances of the button from the neutral position;

(e) a plurality of stationary electrical contacts fixed relative to the housing, wherein the stationary electrical contacts face away from the opening in the housing; and (f) one or more movable electrical contacts secured to a top of the base, wherein a top of the base faces the opening in the housing, wherein the one or more movable electrical contacts is configured to selectively engage the stationary electrical contacts based on movement of the button within a range of motion.

2. The surgical instrument of claim 1, wherein the plurality of stationary electrical contacts are fixed relative to the housing and arranged at sequential radial distances from the neutral position.

3. The surgical instrument of claim 2, wherein the plurality of stationary electrical contacts are arranged in generally dual half-ring configurations centered about the neutral position.

4. The surgical instrument of claim 3, wherein each of the dual half-ring configurations comprise at least two generally concentric half rings.

5. The surgical instrument of claim 4, wherein a first of the dual half-ring configurations is arranged forward of the button and wherein a second of the dual half-ring configurations is arranged backward of the button.

6. The surgical instrument of claim 2, wherein the end effector is activated and controlled by displacement of at least a portion of the input device in either a generally forward or backward direction relative to a longitudinal axis of the handpiece, wherein the generally forward or backward direction includes a lateral range of motion on either side of the longitudinal axis of the handpiece in the forward or backward direction.

7. The surgical instrument of claim 2, wherein each stationary contact is associated with a respective discrete energy level.

8. The surgical instrument of claim 1, wherein the input device further comprises a biasing feature configured to bias the button to the neutral position.

9. The surgical instrument of claim 8, wherein the biasing feature comprises one or more springs, wherein the one or more springs compress or expand based the amount of displacement of the button from the neutral position.

10. The surgical instrument of claim 9, wherein the one or more springs are comprised of molded elastomer.

11. The surgical instrument of claim 1, wherein the one or more movable electrical contacts comprise a metallic ring forming a continuous circle around the post.

12. The surgical instrument of claim 1, wherein the one or more movable electrical contacts are inlaid on the base of the button.

13. The surgical instrument of claim 1, wherein the end effector comprises an ultrasonic blade.

* * * * *